(12) United States Patent
Ogi et al.

(10) Patent No.: US 11,680,137 B2
(45) Date of Patent: Jun. 20, 2023

(54) METHOD FOR PURIFYING TRITYL GROUP-CONTAINING MONODISPERSED POLYETHYLENE GLYCOL

(71) Applicant: NOF CORPORATION, Tokyo (JP)

(72) Inventors: Koichi Ogi, Kawasaki (JP); Takuma Tsubusaki, Kawasaki (JP); Kohei Yoshimura, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 431 days.

(21) Appl. No.: 17/042,331

(22) PCT Filed: Mar. 26, 2019

(86) PCT No.: PCT/JP2019/012867
§ 371 (c)(1),
(2) Date: Sep. 28, 2020

(87) PCT Pub. No.: WO2019/189188
PCT Pub. Date: Oct. 3, 2019

(65) Prior Publication Data
US 2021/0009756 A1    Jan. 14, 2021

(30) Foreign Application Priority Data
Mar. 29, 2018   (JP) ............................. JP2018-063421

(51) Int. Cl.
| | | |
|---|---|---|
| C08G 65/30 | (2006.01) | |
| C08G 65/324 | (2006.01) | |
| C08G 65/329 | (2006.01) | |
| C08G 65/46 | (2006.01) | |
| C08G 65/48 | (2006.01) | |

(52) U.S. Cl.
CPC ........... *C08G 65/30* (2013.01); *C08G 65/324* (2013.01); *C08G 65/329* (2013.01); *C08G 65/46* (2013.01); *C08G 65/48* (2013.01)

(58) Field of Classification Search
CPC .... C08G 65/30; C08G 65/324; C08G 65/329; C08G 65/46; C08G 65/48; C08G 65/337; C08G 65/322; C08G 65/3322; C08G 65/33348; C08G 65/3346; C08G 65/3311; C07C 41/34; C07C 43/11; Y02P 20/55
See application file for complete search history.

(56) References Cited

U.S. PATENT DOCUMENTS

| | | |
|---|---|---|
| 5,298,410 A | 3/1994 | Phillips et al. |
| 2004/0062746 A1* | 4/2004 | Martinez .............. A61K 47/646 530/402 |
| 2010/0292515 A1 | 11/2010 | Yamamoto et al. |
| 2010/0323452 A1 | 12/2010 | Monthony et al. |
| 2011/0040113 A1 | 2/2011 | Wu et al. |
| 2012/0178940 A1 | 7/2012 | Kwiatkowski |
| 2013/0072691 A1 | 3/2013 | Livingston et al. |
| 2016/0075624 A1 | 3/2016 | Yang et al. |
| 2017/0312363 A1 | 11/2017 | Weng et al. |
| 2018/0186931 A1 | 7/2018 | Kinbara et al. |
| 2020/0079905 A1 | 3/2020 | Hirai et al. |
| 2021/0189063 A1 | 6/2021 | Kinbara et al. |

FOREIGN PATENT DOCUMENTS

| | | |
|---|---|---|
| CA | 2 991 011 A1 | 1/2017 |
| CN | 104211943 A | 12/2014 |
| JP | 2005-15341 A | 1/2005 |
| JP | 2008-174755 A | 7/2008 |
| JP | 2012-528857 A | 11/2012 |
| JP | 2013-533900 A | 8/2013 |
| JP | 2015-180698 A | 10/2015 |
| JP | 2017-14371 A | 1/2017 |
| JP | 2018-62655 A | 4/2018 |
| JP | 2018-172645 A | 11/2018 |
| WO | 2008/101311 A1 | 8/2008 |
| WO | 2008/112288 A2 | 9/2008 |
| WO | 2010/033195 A1 | 3/2010 |
| WO | 2010/141069 A2 | 12/2010 |
| WO | 2011/011543 A1 | 1/2011 |
| WO | 2017/002853 A1 | 1/2017 |

OTHER PUBLICATIONS

Stevenson, J.C.; Application of Monodispersed PEGs in Surfactant Molecules, 2017.*
Greene et al.; Protective Groups in Organic Synthesis, 1998, p. 102-104.*
Wawro et al.; Polymer Chemistry, 2016, vol. 7, p. 2389-2394.*
Communication dated Jun. 30, 2021 issued by the Indian Patent Office in corresponding Indian Application No. 202047042015.
Communication issued Dec. 8, 2021 by the European Patent Office in European Patent Application No. 19775170.4.
Dosio et al., "Immunotoxins and Anticancer Drug Conjugate Assemblies: The Role of the Linkage between Components," Toxins, vol. 3, pp. 848-883, 2011.
Zhao et al., "Synthesis and Evaluation of Hydrophilic Linkers for Antibody-Maytansinoid Conjugates," Journal of Medicinal Chemistry, vol. 54, pp. 3606-3623, 2011.
International Search Report dated Jun. 4, 2019 (PCT/ISA/210) issued by the International Searching Authority for International Application No. PCT/JP2019/012867.
Written Opinion dated Jun. 4, 2019 (PCT/ISA/237) issued by the International Searching Authority for International Application No. PCT/JP2019/012867.
Communication dated Oct. 18, 2022 by the China National Intellectual Property Administration for Chinese Patent Application No. 201980023833.0.

(Continued)

*Primary Examiner* — Robert S Jones, Jr.
(74) *Attorney, Agent, or Firm* — Sughrue Mion, PLLC

(57) ABSTRACT

A method for purifying a specific trityl group-containing monodispersed polyethylene glycol from a mixture containing the trityl group-containing monodispersed polyethylene glycol and a specific ditritylated impurity. The method includes performing steps (A), (B) and (C). Step (A): a step of esterifying the hydroxyl group of the trityl group-containing monodispersed polyethylene glycol by a specific method; Step (B): a step of extracting the esterified compound by a specific method; and Step (C): a step of hydrolyzing the esterified compound to obtain the trityl group-containing monodispersed polyethylene glycol.

20 Claims, 20 Drawing Sheets

(56) References Cited

OTHER PUBLICATIONS

Office Action dated Jul. 26, 2022 by the Japan Patent Office in counterpart Japanese Patent Application No. 2019-057912.
Wawro et al., "Chromatography-free synthesis of monodisperse oligo(ethylene glycol) mono-p-toluenesulfonates and quantitative analysis of oligomer purity," Polymer Chemistry, vol. 7, pp. 2389-2394, 2016.

\* cited by examiner

FIG. 2 EXAMPLE 1 RESULTS OF NMR MEASUREMENT OF COMPOUND 2'

FIG. 4 EXAMPLE 3 RESULTS OF NMR MEASUREMENT OF COMPOUND 5'

FIG. 5  EXAMPLE 5  RESULTS OF NMR MEASUREMENT OF COMPOUND 8

FIG. 7  EXAMPLE 6  RESULTS OF NMR MEASUREMENT OF COMPOUND 5 AFTER PURIFICATION

FIG. 8 EXAMPLE 6 TLC CHART OF COMPOUND 5 BEFORE AND AFTER PURIFICATION

FIG. 9 EXAMPLE 7 RESULTS OF NMR MEASUREMENT OF COMPOUND 10 BEFORE LIQUID-SEPARATION WASHING (AFTER COMPLETION OF STEP A)

FIG. 10 EXAMPLE 7 RESULTS OF NMR MEASUREMENT OF COMPOUND 10 AFTER LIQUID-SEPARATION WASHING (AFTER COMPLETION OF STEP B)

FIG. 11 EXAMPLE 7 RESULTS OF NMR MEASUREMENT OF COMPOUND 8 AFTER PURIFICATION (AFTER COMPLETION OF STEP C)

FIG. 12   EXAMPLE 7   TLC CHART OF COMPOUND 8 BEFORE AND AFTER PURIFICATION

FIG. 13 EXAMPLE 11 RESULTS OF NMR MEASUREMENT OF COMPOUND 14

FIG. 14   EXAMPLE 11   RESULTS OF NMR MEASUREMENT OF COMPOUND 14'

FIG. 15  EXAMPLE 13  RESULTS OF NMR MEASUREMENT OF COMPOUND 17

FIG. 16  EXAMPLE 13 RESULTS OF NMR MEASUREMENT OF COMPOUND 17'

FIG. 17  EXAMPLE 15  RESULTS OF NMR MEASUREMENT OF COMPOUND 20

FIG. 18  EXAMPLE 15  RESULTS OF NMR MEASUREMENT OF COMPOUND 20'

FIG. 19 EXAMPLE 16 RESULTS OF NMR MEASUREMENT OF COMPOUND 20 AFTER PURIFICATION

EXAMPLE 16 TLC CHART OF COMPOUND 20 BEFORE AND AFTER PURIFICATION

METHOD FOR PURIFYING TRITYL GROUP-CONTAINING MONODISPERSED POLYETHYLENE GLYCOL

CROSS-REFERENCE TO RELATED APPLICATIONS

This application is a National Phase Entry of PCT International Application No. PCT/JP2019/012867, filed on Mar. 26, 2019, which claims priority to Japanese Patent Application No. 2018-063421 filed on Mar. 29, 2018.

TECHNICAL FIELD

The present invention relates to a purification method for producing a monodisperse polyethylene glycol (PEG) for use in pharmaceutical use efficiently in high purity. More specifically, the invention relates to a method for removing a ditritylated impurity generated by a PEG chain length extension reaction, which is peculiar to monodispersed PEG synthesis.

BACKGROUND ART

A PEG, which improves circulation in blood of a drug through modification thereof, has been widely used in the drug delivery system (DDS) and pharmaceutical fields. In recent years, such a PEG is required to have higher purity from the viewpoint of performance and safety at the time of modification of a drug.

On the other hand, a PEG is a heterogeneous mixture having multiple molecular weights, which is synthesized by ring-opening polymerization of ethylene oxide. On the other hand, a monodispersed PEG, which is sequentially synthesized from a raw material such as low-molecular-weight ethylene glycol, is a single compound having a single molecular weight, and is a novel DDS material characterized by high purity. Since the monodispersed PEG is sequentially synthesized, the labor required for extension of the chain length is vexatious as compared to the case of a conventional PEG synthesized by the ring-opening polymerization, and a low-molecular-weight compound having an ethylene glycol chain length number of 48 or less is commonly used.

In recent years, an antibody-binding drug (Antibody-Drug Conjugate: ADC), in which a drug and an antibody are bound via a linker and which can actively transport the drug to an antigen-presenting cell has been put into practical use and has attracted much attention. (Non-Patent Literatures 1 and 2).

One of the materials currently being utilized as linker materials for the ADC is a hetero-type monodispersed PEG. Since the hetero-type monodispersed PEG is a monodispersed PEG having functional groups different from each other at both terminals, an antibody and a drug can be bound to each terminal. However, when a monodispersed PEG having the same functional group at both terminals is present in the hetero-type monodispersed PEG, an impurity in which two antibodies are bound or an impurity in which two drugs are bound are produced. The presence of these impurities lowers the yield of the target ADC, and therefore, a highly pure hetero-type monodispersed PEG is required in this field.

Moreover, at the time of manufacturing ADC, since the number of drugs bound is usually confirmed using a mass spectrometer or HPLC (high performance liquid chromatography), when a monodispersed PEG having a different ethylene glycol chain length is present as an impurity in the linker material, there arises a manufacturing problem that the confirmation thereof becomes difficult. In addition, resulting from the presence of the impurity having a different ethylene glycol chain length, there are a problem that, since equivalents of the antibody and the drug to be added at the time of manufacturing ADC become unclear, it becomes necessary to excessively use expensive antibody and drug and a problem that compounds having a plurality of molecular weights are formed at the application for drug and thus the identification of compounds and performance of various tests become necessary. Therefore, it can be said that, as the hetero-type monodispersed PEG, it is important to contain only one kind of monodispersed PEG having the same ethylene glycol chain length with high purity.

As above, the hetero-type monodispersed PEG to be used as a linker material of ADC is desired to be one containing a hetero-type monodispersed PEG having different functional groups at both terminals as main components, which is a monodispersed PEG having a uniform ethylene glycol chain length, particularly with high purity.

In general, it is known that, in the chain length extension step of a monodispersed PEG, an ethylene glycol derivative having a protective group for a hydroxyl group such as a trityl group that is a bulky hydrophobic group is used as a raw material. Further, in each step for extending the chain length of the monodispersed PEG, impurities having different chain length numbers or different functional groups are formed. However, unlike a high-molecular-weight PEG, a low-molecular-weight monodispersed PEG is greatly affected by a functional group, and is liquid in many cases, so that simple crystallization purification specific to a polymer cannot be frequently performed. Therefore, many of these impurities remain in the target substance. Further, in the chain length extension step, there is no clear polarity difference between the target substance and the impurities, and it is difficult to separate them by any industrially applicable purification method.

Although there are a plurality of reports on the method for producing a monodispersed PEG, in Patent Literature 1, the chain length of a monodispersed PEG is extended by the following method.

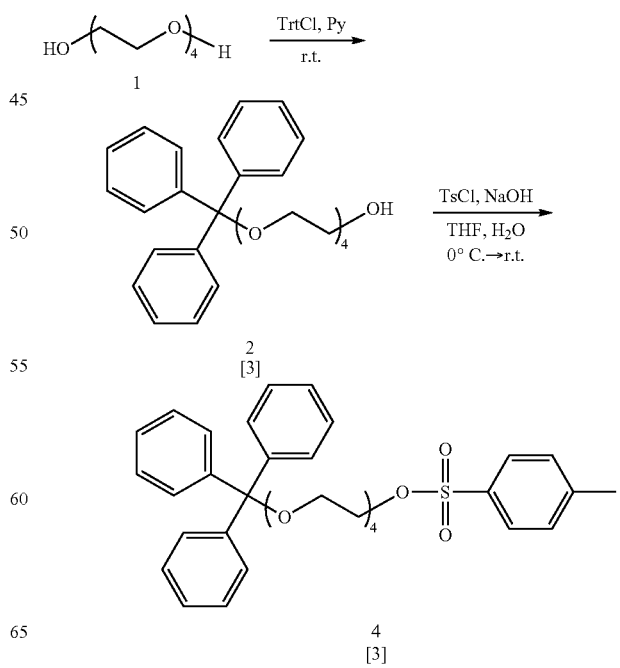

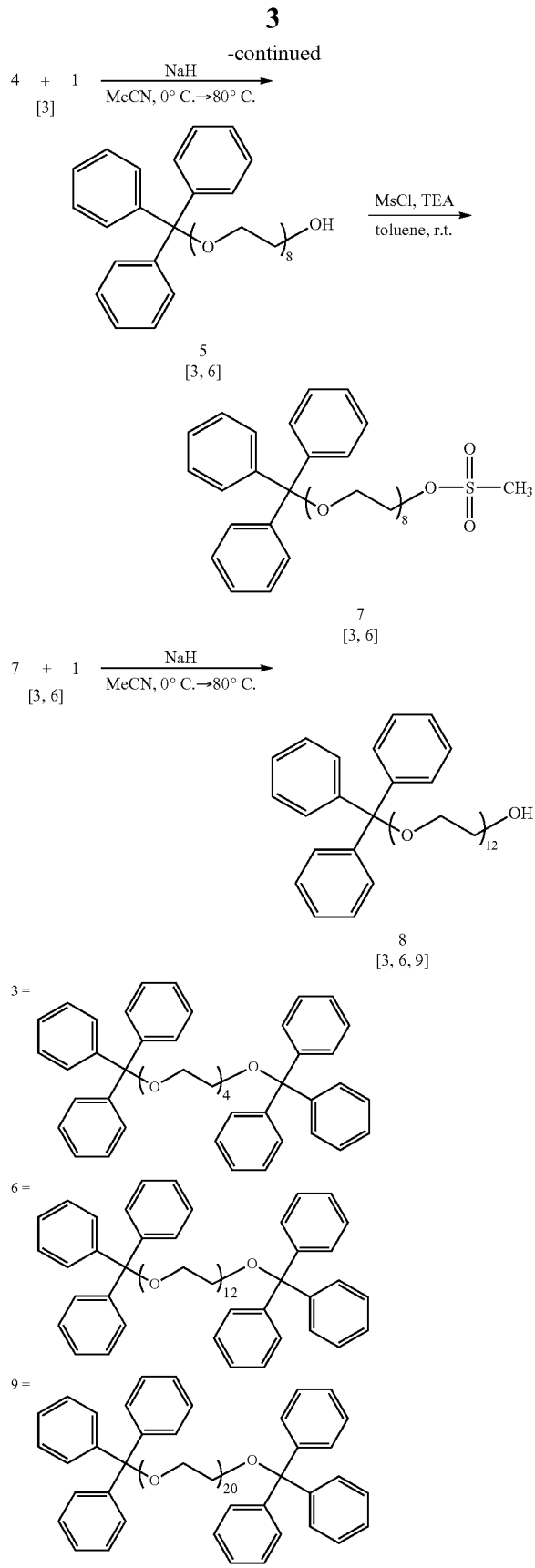

As above, in this chain length extension step, the compound 8 which is the target monodispersed PEG of dodecamer contains ditritylated impurities 3, 6, and 9. Since these impurities have physical properties similar to those of the target substance, it is difficult to remove them and the purification method is limited to a purification method such as column chromatography which is not suitable for scale-up. Further, Patent Literature 1 does not describe a purification method for removing these ditritylated impurities from the compound 8.

In Patent Literature 1, after the hydroxyl group of the compound 8 is converted into a tosyl group which is a bulky hydrophobic group, the impurities 3, 6, and 9 which have subjected to a detritylation reaction and converted into diol compounds are removed by liquid-separation extraction.

PRIOR ART DOCUMENTS

Non-Patent Literatures

Non-Patent Literature 1: Toxins, 2011, 3, p. 848-883
Non-Patent Literature 2: J. Med. Chem., 2011, 54, p. 3606-3623

Patent Literature

Patent Literature 1: JP-A-2017-14371

SUMMARY OF INVENTION

Problem to be Solved by the Invention

From the above, in the existing industrially applicable purification methods, in order to remove a ditritylated impurity, it is necessary to once perform the conversion into a bulky hydrophobic group such as a tosyl group. However, in the case where it is purposed to obtain a compound that does not require this bulky hydrophobic group in the original functional group conversion step, a problem is that the addition of a series of steps for removing the ditritylated impurity makes the synthesis process complicated and reduces the efficiency of synthesis.

On the other hand, after the hydroxyl group of the compound 8 was converted into a hydrophobic group having low hydrophobicity such as a methyl group, when an attempt of the above detritylation reaction of Patent Literature 1 and removal of the impurities 3, 6, and 9 which had become diol bodies was made, it was not possible to separate the diol body impurities from the target substance by liquid-separation extraction. As described above, it becomes obvious that a ditritylated impurity cannot be removed by the method of Patent Literature 1 depending on the functional group to be added.

Moreover, in the case of carrying out a reaction using a monodispersed PEG containing a ditritylated impurity, there is no suitable method for accurately calculating the purity of the raw material monodispersed PEG and hence the appropriate amount of the reagent to be used in the reaction cannot be determined. Further, when the amount of the impurity varies, an equivalent reaction cannot always be performed, and there is a risk that side reactions will occur due to excess reagents or the reaction will not be completed due to insufficient reagents. Also, the purity of the product obtained becomes unclear. In addition, an adverse influence is exerted on the purification operation by liquid-separation extraction which is commonly used as a purification operation of a monodispersed PEG. Ditritylated impurities having different chain lengths show different hydrophilicity/hydrophobicity from each other, and the layer separation property is decreased, so that a decrease in extraction efficiency may be invited.

From the above, there is a demand for a method for efficiently removing a ditritylated impurity which is contained in a monodispersed PEG and has a specific molecular weight derived from the chain extension step.

The present invention relates to purification of a specific ditritylated impurity having a different chain length, which is produced as a by-product in the chain length extension step of a monodispersed PEG. That is, an object of the invention is to provide a purification method capable of efficiently obtaining a highly pure monodispersed PEG suitable for pharmaceutical use, by an industrially applicable method.

Means for Solving the Problem

As a result of extensive studies for solving the above problems, the present inventors have found that, with regard to a mixture obtained after the chain length extension step of a monodispersed PEG, after hydrophilicity is increased by esterifying the hydroxyl group of a one-terminal trityl group-containing monodispersed PEG to introduce a carboxylic acid, an extraction operation of a specific composition is repeated and thereby a ditritylated impurity can be extracted and removed into the organic layer. Furthermore, it has been found that a highly pure one-terminal trityl group-containing monodispersed PEG can be rapidly obtained by subsequently hydrolyzing the ester group of the one-terminal trityl group-containing monodispersed PEG derivative in the aqueous layer.

The feature of the invention is that the carboxylic acid can be efficiently introduced into the one-terminal trityl group-containing monodispersed PEG, the ditritylated impurity can be removed into the organic layer by controlling specific pH, a specific mixing ratio of a hydrocarbon solvent to an aromatic solvent, and extraction temperature at the time of extraction purification, and the three steps including the subsequent hydrolysis step can be carried out continuously in a series of processes, and the invention is an industrially applicable and efficient purification method.

Thus, the present invention is as follows.
(1) A method for purifying a trityl group-containing monodispersed polyethylene glycol, which include, from a mixture containing a trityl group-containing monodispersed polyethylene glycol represented by the following formula (1) and a ditritylated impurity represented by the following formula (2), separating and removing the ditritylated impurity to obtain the trityl group-containing monodispersed polyethylene glycol, the method comprising performing steps (A), (B) and (C) in this order:

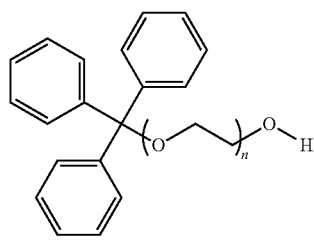

(1)

wherein, in the formula (1), n is the number of repeating units of an ethylene oxide unit and is 3 or more and 48 or less;

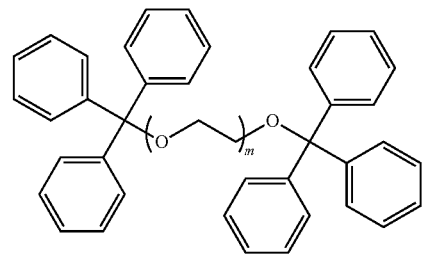

(2)

wherein, in the formula (2), r is the number of repeating units of an ethylene oxide unit and is 3 or more and 92 or less;

Step (A): a step of obtaining a reaction solution containing an ester compound having an ester structure and a carboxyl group by reacting the hydroxyl group of the trityl group-containing monodispersed polyethylene glycol represented by the formula (1) with a dibasic acid anhydride in the following organic solvent II, Step (B): an extraction step of separating an aqueous layer and an organic layer, partitioning the ditritylated impurity represented by the formula (2) into the organic layer and partitioning the ester compound into the aqueous layer by performing liquid-separation extraction purification using the reaction solution obtained in the step (A), one or more organic solvents selected from the group consisting of the following organic solvents I, II and III, and an aqueous solution having a pH of 3 to 7, Step (C): a step of performing hydrolysis of the ester compound by adding a base to the aqueous layer to obtain the trityl group-containing monodispersed polyethylene glycol:

Organic solvent I: an alcohol solvent having 3 or less carbon atoms,

Organic solvent II: an aromatic hydrocarbon solvent having 8 or less carbon atoms in total, Organic solvent III: a saturated aliphatic hydrocarbon solvent having 10 or less carbon atoms in total.

(2) The method according to (1), wherein in the step (A), the dibasic acid anhydride is selected from the group consisting of succinic anhydride and glutaric anhydride.

(3) The method according to (1) or (2), wherein in the step (B), the organic solvent I is one or more solvents selected from methanol, ethanol and propanol, the organic solvent II is one or more solvents selected from the group consisting of toluene and xylene, and the organic solvent III is one or more solvents selected from the group consisting of pentane, hexane and heptane.

(4) The method according to any one of (1) to (3), wherein with regard to the mixing ratio of the organic solvent in the step (B), the mass ratio of the organic solvent I is from 15 to 55% by mass, the mass ratio of the organic solvent II is from 15 to 75% by mass, and the mass ratio of the organic solvent III is from 0 to 50% by mass.

(5) The method according to any one of (1) to (4), wherein the temperature during the extraction step of the step (B) is 0° C. or higher and 60° C. or lower.

(6) The method according to any one of (1) to (5), wherein the extraction step of the step (B) is repeated.

(7) The method according to any one of (1) to (6), wherein the base in the step (C) is one or more bases selected from the group consisting of sodium hydroxide and potassium hydroxide.

Effect of the Invention

The present invention is a novel purification method of obtaining a highly pure monodispersed PEG suitable for pharmaceutical use. In this purification method, a one-terminal trityl group-containing monodispersed PEG (formula (1)) and a ditritylated impurity of a specific molecular weight having a different chain length (formula 2), which are formed in the chain length extension step and are difficult to efficiently separate by a conventional technique, can be efficiently separated by derivatization of the terminal hydroxyl group and extraction purification. Further, the derivatized functional group portion can be promptly eliminated still in an aqueous solution state after purification and can be restored to the original structure before the derivatization. That is, it is possible to obtain a highly pure one-terminal trityl group-containing monodispersed PEG in which the ditritylated impurity is remarkably reduced, in high yield by a continuous process that can be easily carried out industrially.

Moreover, according to the present invention, the one-terminal trityl group-containing monodispersed PEG can be purified and isolated, and therefore, in the functional group conversion step of the next step which has been hitherto carried out in a state that the ditritylated impurity is contained, it is possible to produce a monodispersed PEG derivative in high purity and high yield with good reproducibility.

MODES FOR CARRYING OUT THE INVENTION

Figure 1:
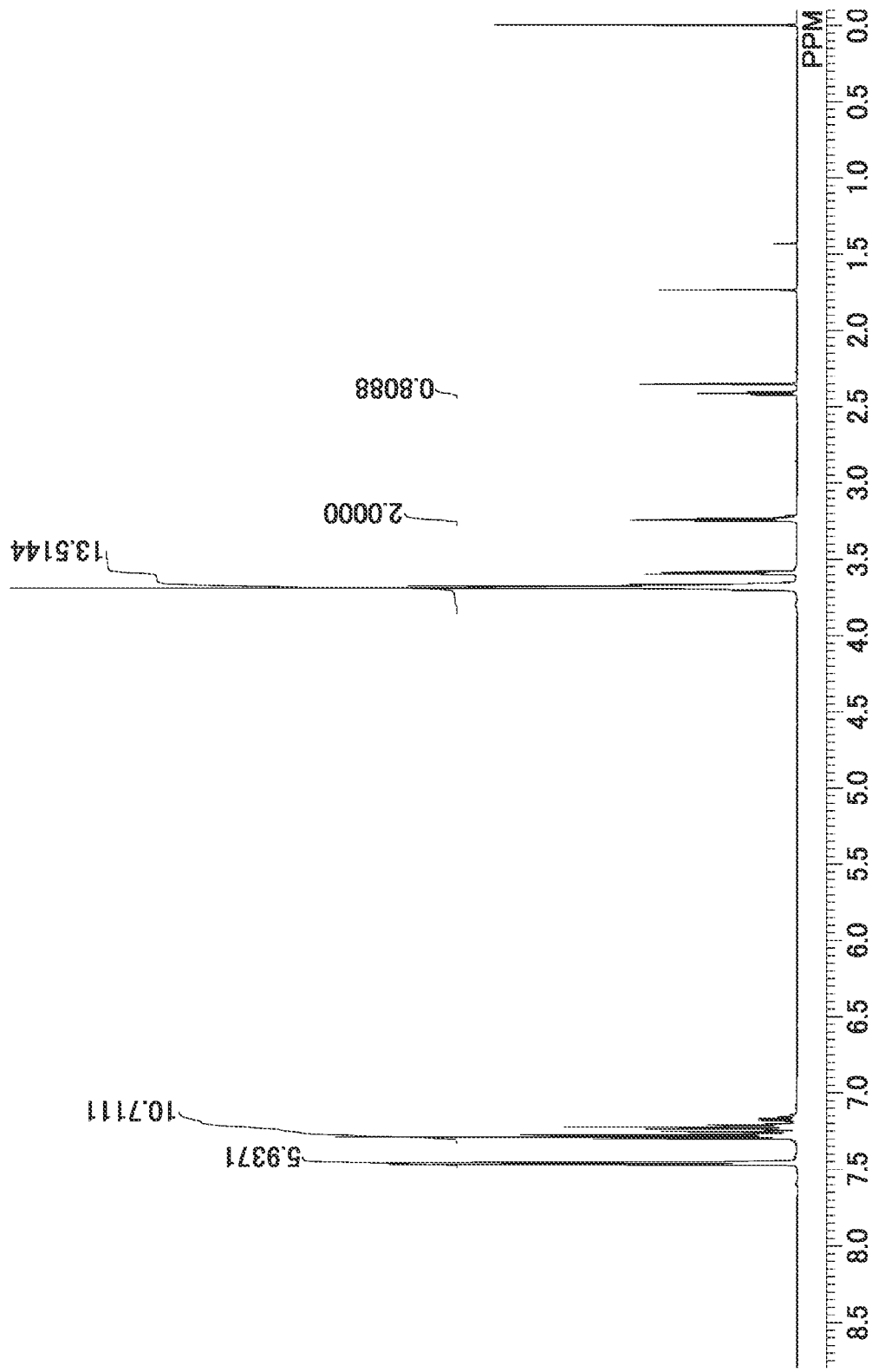
FIG. 1 shows results of NMR measurement of the compound 2 in Example 1.

The PEG compound in the present invention is a general term for compounds having a repeating structure of an ethylene glycol chain. Further, PEG refers to a mixture of a large number of PEG compounds having a plurality of molecular weights, which is obtained by ring-opening polymerization of ethylene oxide. In contrast, a monodispersed PEG is a PEG compound having a single molecular weight, the target PEG compound being obtained by sequential synthesis using ethylene glycol as a raw material. In other words, the monodispersed PEG is a PEG compound in which the ethylene glycol chain length number (the number of repeating units of an ethylene oxide unit) is single.

In the chain length extension step of the monodispersed PEG, a general chain length extension reaction is performed using a trityl group as a protective group for the hydroxyl group. At the time of the chain length extension, there is obtained a mixture of a target one-terminal trityl group-containing monodispersed PEG, which has one trityl group and has a hydroxyl group at another terminal, and a ditritylated impurity that is a monodispersed PEG having a specific chain length number, in which both terminals are trityl groups. According to the invention, the ditritylated impurity of the formula (2) is separated from this mixture to obtain the one-terminal trityl group-containing monodispersed PEG of the formula (1).

The following will describe preferred conditions for carrying out the invention. However, these embodiments are described for the purpose of illustrating the invention and should not be construed as limiting the scope of the invention as defined by Claims.

The ethylene glycol chain length number n of the one-terminal trityl group-containing monodispersed PEG of the invention is 3 or more and 48 or less, preferably 4 or more and 24 or less, more preferably 4 or more and 20 or less, and particularly preferably 8 or more and 12 or less. The chain length number m of the corresponding ditritylated impurity is 3 or more and 92 or less, preferably 4 or more and 44 or less, more preferably 4 or more and 36 or less, and particularly preferably 4 or more and 20 or less.

The one-terminal trityl group-containing monodispersed PEG of the invention is a linear monodispersed PEG having no branched structure.

The organic solvents to be used at the time of the liquid-separation extraction of the invention are classified into the following organic solvents I to III in the order from a solvent having a strong hydrophilicity to a solvent having a weak hydrophilicity.

Organic Solvent I:

A water-soluble and hydrophilic alcohol solvent having 3 or less carbon atoms in total, such as methanol, ethanol, propanol or isopropanol, preferably methanol, ethanol or propanol, more preferably methanol.

Organic solvent II:

An aromatic hydrocarbon solvent having 8 or less carbon atoms in total, such as benzene, toluene or xylene, preferably toluene or xylene, more preferably toluene.

Organic Solvent II:

A saturated aliphatic hydrocarbon solvents having 10 or less carbon atoms in total, such as pentane, hexane, heptane, octane, nonane or decane, preferably pentane, hexane or heptane, more preferably hexane.

Step (A)

The step is an esterification reaction step in which the hydroxyl group of the one-terminal trityl group-containing monodispersed PEG in the monodispersed PEG mixture obtained in the chain extension step is converted into a dibasic acid ester using a dibasic acid anhydride. The obtained ester compound has an ester structure and a carboxyl group.

The esterification reaction is carried out using a dibasic acid anhydride and a base catalyst.

The dibasic anhydride to be used is a dibasic acid anhydride such as succinic anhydride, glutaric anhydride, adipic anhydride, methylsuccinic anhydride, methylglutaric anhydride, maleic anhydride, phthalic anhydride, and tartaric anhydride. In order to improve the hydrophilicity of the one-terminal trityl group-containing monodispersed PEG, succinic anhydride and glutaric anhydride that have a methylene chain having 3 or less carbon atoms at the ring opening and have no branched chain is preferable and succinic anhydride is more preferable. The dibasic acid anhydride is ring-opened by the action of water contained in the solvent and the raw material to form a dibasic acid, so that it is preferable to add the anhydride in small excess. Usually, the molar ratio is from 1.0 to 3.0 times, and more preferably from 1.0 to 2.0 times. When the excess amount is large, the acidity of the aqueous solution increases in the subsequent extraction step, and there is a risk of elimination of the trityl group.

The base catalyst is preferably added in a molar ratio of 0.01 to 1.0 times, preferably 0.5 to 1.0 times, relative to the one-terminal trityl group-containing monodispersed PEG. Since the basic catalyst is consumed for neutralization of the dibasic acid formed by the ring opening of the dibasic acid anhydride with water, the reaction tends to be slow when the addition amount of the catalyst is small. Further, when the basic catalyst is insufficient and the amount of the dibasic acid in the solution increases, there is a risk of elimination of the trityl group.

The esterification reaction can be carried out in a solvent, and a solvent selected from the organic solvent II is used. The amount of the solvent to be used is preferably from 1.0 to 2.0 times by mass, relative to the one-terminal trityl group-containing monodispersed PEG.

The esterification reaction is usually performed between 0° C. and 120° C., preferably 30° C. and 110° C., and more preferably 50° C. and 80° C. When the temperature is low, the reaction rate tends to be low, and when it is high, the trityl group tends to be eliminated. The reaction time varies depending on the reaction conditions, but is usually preferably approximately from 1 to 48 hours.

After the reaction, the dibasic acid derived from the dibasic acid anhydride and the base catalyst remaining in the solution may be removed. In that case, after diluting the reaction solution with the organic solvent II, extraction is performed with a saline solution having an adjusted salt concentration to remove the dibasic acid and the basic catalyst into the aqueous layer.

The salt concentration of the aqueous solution is not particularly limited as far as there is no distribution of the monodispersed PEG into the aqueous layer, but is usually from 5 to 25% by mass, preferably from 15 to 25% by mass based on the added aqueous solution. The extraction temperature is usually in the range of 10° C. to 80° C., preferably 30° C. to 60° C. in order to improve the layer separation property of each solution. When the extraction temperature is low, the distribution of the monodispersed PEG ester compound into the aqueous layer is improved and emulsification tends to occur. When the extraction temperature is high, the trityl group tends to be eliminated.

In the step (A), a dibasic acid ester of the one-terminal trityl group-containing monodispersed PEG containing a carboxylic acid terminal is obtained by such an esterification reaction. In the case where succinic anhydride or glutaric anhydride is used as the dibasic acid anhydride, a mixture of the monodispersed PEG ester compound (carboxylic acid derivative) having a structure represented by the formula (3) and the ditritylated impurity is obtained. This ester compound has an ester structure and a carboxyl group.

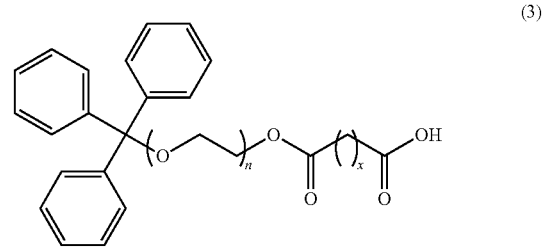

(3)

(n is the number of repeating units of ethylene oxide units and is an integer of 3 or more and 48 or less; x is an integer that varies depending on the dibasic acid anhydride used and is 2 or 3.)

In the case where the elimination of the trityl group in the step (A) occurs at the terminal of the ditritylated impurity during the esterification reaction, a monodispersed PEG ester compound having a different ethylene glycol chain length is produced as a by-product, and thus care must be taken because the compound becomes a new impurity that cannot be separated by the invention.

Step (B)

The step is a step in which one or more organic solvent selected from the group consisting of the organic solvents I, II, and III and an aqueous solution are added to the mixture solution obtained in the step (A), the whole is mixed by stirring or shaking and allowed to stand for a certain period of time, and thereby the monodispersed PEG ester compound is separated into the aqueous layer and the ditritylated impurity is separated into the organic layer to perform extraction purification.

The monodispersed PEG ester compound contains a trityl group that is hydrophobic and a carboxylic acid that is hydrophilic, and exhibits a solubility characteristic of an amphipathic compound. Therefore, the monodispersed PEG ester compound is unlikely to form a homogeneous solution in water/organic solvents other than a hydrophilic organic solvent, although it depends on the ethylene glycol chain length number. On the other hand, the ditritylated impurity that is a target to be separated has only a hydrophobic functional group, but since it exhibits hydrophilicity derived from the ethylene glycol chain, it is also soluble in a hydrophilic solvent. The solubility of each one is as follows. Solubility of Monodispersed PEG Ester Compounds.

Organic solvent I>Organic solvent II≈Water>>>Organic solvent III Solubility of ditritylated impurities.

Organic solvent I>Organic solvent II>Organic solvent III>Water

In order to extract the monodispersed PEG ester compound into the aqueous layer, it is necessary to ionize the carboxylic acid to improve the water solubility. However, even when it is ionized, it is difficult to be homogeneously dissolved in the aqueous layer as described above and an emulsified state is formed. For suppressing the emulsification, addition of the organic solvent I or heating, or addition of the organic solvent I and heating are needed.

On the other hand, the dibasic acid ester moiety of the monodispersed PEG ester compound is easily hydrolyzed under basic conditions. As a result, the compound is decomposed into the raw material one-terminal trityl group-containing monodispersed PEG, which is distributed to the organic layer by the subsequent extraction operation and is lost.

From the above, the pH of the aqueous solution to be used for liquid-separation extraction purification of the monodispersed PEG ester compound is a weakly acidic to neutral condition of pH3 to 7, preferably pH 5 to 7. The aqueous layer in which the monodispersed PEG ester compound is dissolved is under a weak acidic to neutral condition of pH 3 to 7, preferably pH 5 to 7.

In order to ionize the monodispersed PEG ester compound, a pH-adjusted aqueous solution is added as an aqueous layer. The salt to be used for adjusting the pH is not particularly limited as far as it can ionize the carboxylic acid, but includes usually organic salts and inorganic salts such as phosphates, acetates, carbonates, bicarbonates, borates, citrates, phthalates, tartrates or lactates. Further, a plurality of these organic salts and inorganic salts may be used in combination.

The concentration of the salt is not particularly limited as far as the pH of the aqueous solution to be used for liquid-separation extraction purification of the monodispersed PEG ester compound is from 3 to 7. When the salt concentration is too high, the monodispersed PEG ester compound cannot be retained in the aqueous layer during extraction washing with an organic solvent, and a salt is precipitated at the time of mixing with the organic solvent I to be mentioned later. Therefore, the concentration is 10% by mass or less, preferably 5% by mass or less based on water.

The solubility of the ionized monodispersed PEG ester compound becomes as follows: Organic solvent I>Aqueous solution>Organic solvent II>>>Organic solvent III. On the other hand, the solubility of the ditritylated impurity is as follows: Organic solvent I>Organic solvent II>Organic solvent III>Aqueous solution. As a result, the difference in distribution of each compound between the aqueous layer and the organic layer becomes clear, and the purification by liquid-separation extraction becomes possible.

In order to separate the ditritylated impurity, it is necessary to extract the ditritylated impurity from the aqueous layer using the organic solvent II. However, the monodispersed PEG ester compound is also soluble in the organic solvent II, and the loss of the monodispersed PEG ester compound occurs when only the organic solvent II is used as the organic layer. Therefore, the organic solvent I in which the monodispersed PEG ester compound is insoluble is added to reduce the loss of the monodispersed PEG ester compound, and thereby it becomes possible to improve the selectivity of the ditritylated impurity to extract and separate the ditritylated impurity into the organic layer efficiently.

The preferred mixing ratio of each organic solvent depends on the ethylene glycol chain length number of the monodispersed PEG to be purified. The shorter the ethylene glycol chain length of the monodispersed PEG ester compound is, the stronger the influence of the trityl group that is hydrophobic is. Thus, it becomes difficult to retain the compound in the aqueous layer. Therefore, it is necessary to increase the mixing ratio of the organic layer I and the organic layer III as the chain length becomes short.

On the other hand, as the ethylene glycol chain length becomes long, the ditritylated impurity is more strongly influenced by the hydrophilic ethylene glycol chain, the hydrophobicity decreases, and the affinity for the aqueous layer increases. Therefore, as the chain length becomes long, it is necessary to increase the mixing ratio of the organic solvent II to increase the extraction efficiency of the ditritylated impurity to the organic layer side.

The amount of the aqueous solution at the time of extraction is usually from 0.5 to 10 times by mass, preferably from 1 to 5 times by mass, relative to the raw material monodispersed PEG compound. The amount of the solvent in the case where the organic solvent I is added for suppressing the emulsification of the aqueous layer is usually from 0.3 to 4 times by mass, more preferably from 0.8 to 2.4 times by mass, relative to the aqueous layer. The total mass of the organic solvents II and III or the solution composed of the organic solvent II is usually from 0.3 to 2 times, more preferably from 0.7 to 1.2 times the total mass of the aqueous solution or the aqueous solution and the solution composed of the organic solvent I.

The mixing ratio of the organic solvent is preferably organic solvent I: 0 to 55%, organic solvent II: 15 to 75%, organic solvent III: 0 to 50% (all % by mass), and more preferable mixing ratio is organic solvent I: 15 to 55%, organic solvent II: 15 to 75%, organic solvent III: 0 to 50% (all % by mass).

The preferred mixing ratio for each chain length is as follows: in case of ethylene glycol chain length of 3 to 7, organic solvent I: 25 to 55%, organic solvent II: 15 to 45%, organic solvent III: 20 to 50% (all % by mass), and more preferred is organic solvent I: 35 to 45%, organic solvent II: 25 to 35%, organic solvent III: 30 to 40% (all % by mass).

In case of an ethylene glycol chain length of 8 to 24, the mixing ratio is preferably organic solvent I: 20% to 50%, organic solvent II: 30% to 70%, organic solvent III: 0% to 45% (all % by mass), more preferably organic solvent I: 25 to 45%, organic solvent II: 40 to 60%, organic solvent III: 5 to 25%, and further preferably organic solvent I: 27.5 to 32.5%, organic solvent II: 47.5 to 52.5%, organic Solvent III: 17.5 to 22.5% (all % by mass).

In case of the ethylene glycol chain length of 25 to 48, the mixing ratio is preferably organic solvent I: 0 to 45%, organic solvent II: 45 to 75%, organic solvent III: 0 to 35% (all % by mass), and more preferable organic solvent 1: 25-35%, organic solvent II: 55-65%, organic solvent III: 15-25% (all % by mass).

The temperature at the time of the extraction purification is usually from 0 to 60° C., preferably from 30 to 60° C., and more preferably from 45 to 55° C., because the emulsification cannot be avoided when the temperature is low and the organic solvent is evaporated when it is too high.

Step (C)

The step is a step in which a base is added to the aqueous layer after extraction, the dibasic acid ester is hydrolyzed to restore the monodispersed PEG ester compound to the one-terminal trityl group-containing monodispersed PEG, and then the monodispersed PEG is extracted into an organic layer and collected.

A base is added to an aqueous solution containing the monodispersed PEG ester compound to perform hydrolysis. It is preferable that a basic compound is added to the aqueous solution, the pH of the aqueous layer is maintained to 9 or higher to perform a hydrolysis reaction under basic conditions, and thus the ester is decomposed.

The base to be used in the hydrolysis reaction is not limited as far as it can adjust the pH to 9 or higher, but is preferably a strong base having nucleophilicity. Specifically, it is sodium hydroxide or potassium hydroxide, more preferably sodium hydroxide.

An organic solvent is added to the aqueous solution after the hydrolysis reaction, and the target substance is extracted into the organic layer to collect the one-terminal trityl group-containing monodispersed PEG. The one-terminal trityl-containing monodispersed PEG is obtained by a step including any one of concentration, crystallization and drying.

The organic solvent to be used at the time of recovering the one-terminal trityl group-containing monodispersed PEG is an organic solvent selected from toluene, xylene, chloroform, dichloromethane and dichloroethane, and is preferably toluene, chloroform or dichloromethane, more preferably toluene.

EXAMPLES

Hereinafter, the present invention will be described in more detail with reference to Examples, but the invention is not limited to the following Examples.

The one-terminal trityl group-containing monodispersed PEG to be used as a raw material of the invention was synthesized in Examples 1 to 5 and 10 to 15 with reference to Patent Literature 1. The obtained one-terminal trityl group-containing monodispersed PEGs of octamer, dodecamer and tetracosamer contained a plurality of ditritylated impurities. Accurate quantitative determination of the content was difficult, but the hydroxyl group of the one-terminal trityl group-containing monodispersed PEG was labeled with trichloroacetyl isocyanate, and the contents of the ditritylated impurities contained in each step were roughly estimated from the results of $^1$H-NMR measurement of the obtained compound. In Examples 6 to 9 and 16, purification of the one-terminal trityl group-containing monodispersed PEGs of octamer, dodecamer and tetracosamer obtained in the above Examples was performed, and removal of the ditritylated impurities was confirmed.

Incidentally, in the reaction of each Example, since the exact number of moles of the one-terminal trityl group-containing monodispersed PEG is unknown, the reagent equivalent was calculated assuming that the entire amount is composed of a one-terminal trityl group-containing monodispersed PEG.

Regarding the measurement of the monodispersed PEG obtained in the invention, JNM-ECP400 or JNM-ECA600 manufactured by JEOL Datum Co., Ltd. was used in $^1$H-NMR analysis. A φ5 mm tube was used for the measurement, CDCl$_3$ was used as a deuterated solvent, and tetramethylsilane (TMS) was used as an internal standard substance.

In TLC analysis, a TLC glass plate Silica Gel 60 F$_{254}$ manufactured by Merck Millipore was used, and chloroform:methanol=85:15 (volume ratio) or chloroform:methanol=9:1 (volume ratio) was used as a developing solvent unless otherwise specified. The spots in the iodine coloration were compared with the spot of the compound used as an authentic specimen and evaluated. For the confirmation of the removal of the ditritylated impurities by the esterification reaction in the step (A) and the liquid-separation extraction in the step B in Examples 6 to 9 and 16, the one-terminal trityl group-containing monodispersed PEG was used as an authentic specimen. A monodispersed PEG ester compound was used for the confirmation of the ester hydrolysis reaction in the step (C).

Example 1 Synthesis of Compound 2

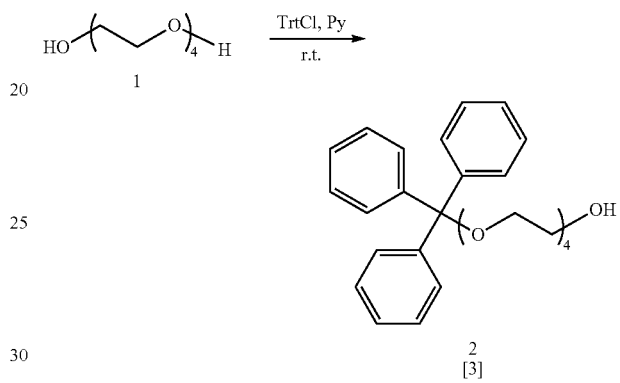

Tetraethylene glycol 1 (2,000 ml, 11.5 mol) was placed in a four-necked flask, and azeotropic dehydration was performed twice using toluene (500 ml×2 times). The inside of the eggplant-shaped flask was purged with nitrogen, pyridine (180 ml, 2.2 mol) and trityl chloride (TrtCl, 400 g, 1.4 mol) were added, and the mixture was stirred at room temperature for 3 hours. After 3 hours, the disappearance of TrtCl was confirmed using thin layer chromatography (TLC, hexane:ethyl acetate=1:1 (volume ratio)), and 2,000 ml of ion-exchanged water was added. After toluene (1,000 ml) was added to the resulting mixture, the layers were separated and the organic layer was washed once with 1,000 ml of a mixed solution of ion-exchanged water/a saturated saline solution (ion-exchanged water:saturated saline solution=4:1 (volume ratio)), once with 500 mL of a 1M aqueous hydrochloric acid solution, and 4 times with 500 ml of a saturated saline solution. Sodium sulfate was added to the obtained organic layer, which was dried and filtered. While adding toluene (500 ml×3 times) to the filtrate, azeotropic dehydration was performed 3 times to obtain a reaction product containing the compound 2 as a pale yellow transparent liquid. Further, it was confirmed from the results of TLC measurement and NMR measurement (FIG. 1) that the obtained reaction product also contained the above compound 3.

Compound 2

$^1$H-NMR (CDCl$_3$, internal standard TMS); δ (ppm):

2.4 (1H, t, —C—(OCH$_2$CH$_2$)$_4$—O$\underline{H}$), 3.23 (2H, t, (C$_6$H$_5$)$_3$C—OC$\underline{H_2}$CH$_2$—, including those derived from compound 3), 3.45-3.85 (14H, m, —OCH$_2$C$\underline{H_2}$—(OC$\underline{H_2}$C$\underline{H_2}$)$_3$—OH, including those derived from compound 3), 7.21-7.47 (15H, m, (C$_6$$\underline{H_5}$)$_3$C—OCH$_2$CH$_2$—, including those derived from compound 3)

Yield: 633 g

[Chem 6]

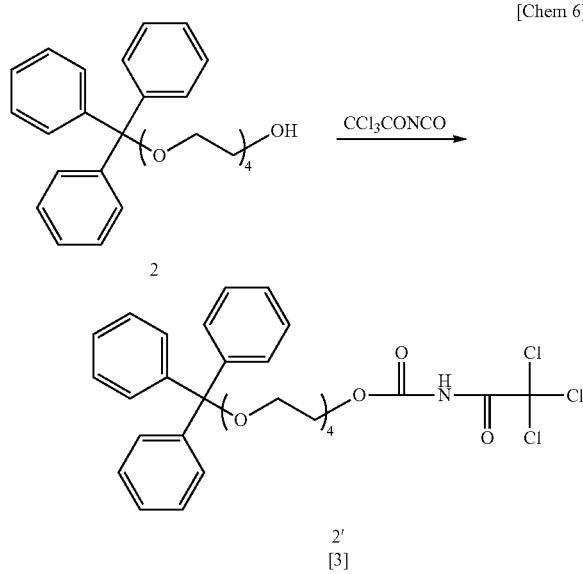

Figure 2:
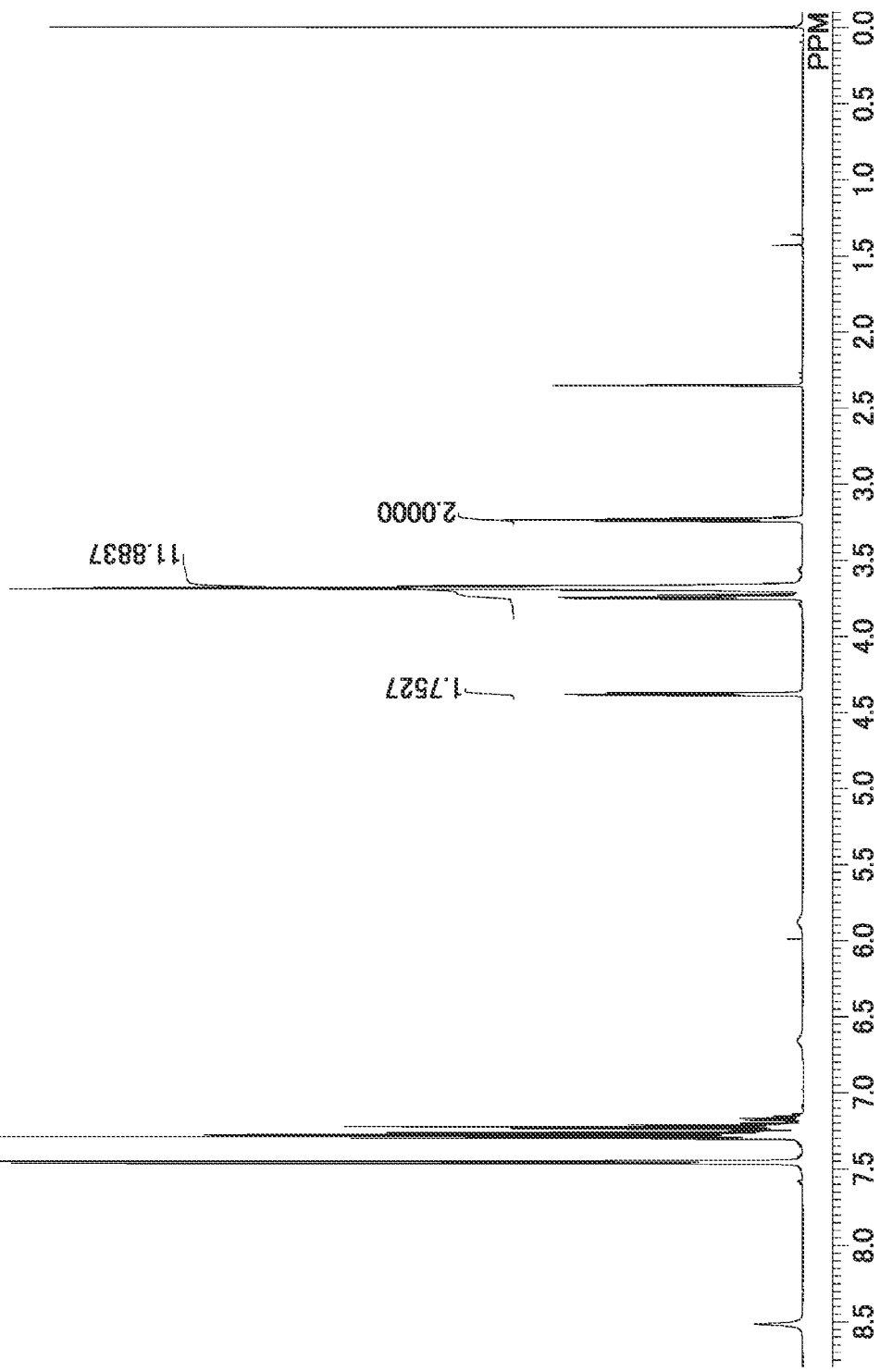
FIG. 2 shows results of NMR measurement of the compound 2' in Example 1.

From the results of $^1$H-NMR measurement (FIG. 2) of the compound 2' in which the hydroxyl group was labelled by treating the obtained reaction product containing the compound 2 using trichloroacetyl isocyanate, it was confirmed that the compound 3 was contained in an amount of about 7 mol %.

Calculation Formula of Content of Compound 3 Based on the Peak at δ 3.23:

(((2−[δ4.38])/4H)/([δ4.38]/2H))×100(mol %)

Compound 2'

$^1$H-NMR (CDCl$_3$, internal standard TMS); δ (ppm):

3.23 (2H, t, (C$_6$H$_5$)$_3$C—OCH$_2$CH$_2$—, including those derived from compound 3), 3.45-3.85 (12H, m, —OCH$_2$CH$_2$—(OCH$_2$CH$_2$)$_2$—OCH$_2$CH$_2$—OCO—, including those derived from compound 3)

4.38 (2H, t, —OCH$_2$CH$_2$—OCO—NH—COCCl$_3$), 7.21-7.47 (15H, m, (C$_6$H$_5$)$_3$C—OCH$_2$CH$_2$—, including those derived from compound 3)

Example 2 Synthesis of Compound 4

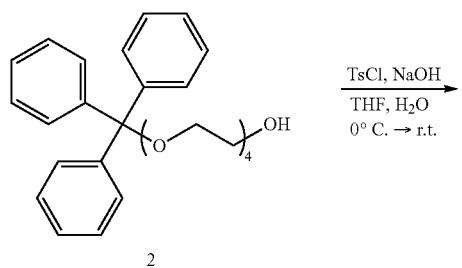

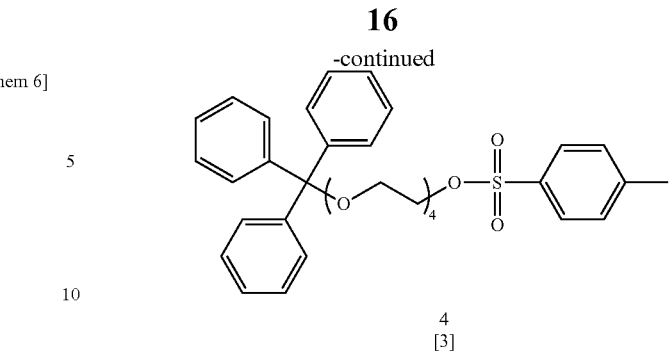

A reaction product containing the above compound 2 (compound 2: 628 g, less than 0.14 mol) and 2.000 ml of tetrahydrofuran (THF) were placed in an eggplant-shaped flask and the whole was cooled to 0° C. An aqueous sodium hydroxide solution (200 g, 5.0 mol/600 ml) was added, followed by stirring at 0° C. for 20 minutes. A tosyl chloride (TsCl)/THF solution (300 g, 1.6 mol/600 ml) was added dropwise to the reaction mixture over a period of 30 minutes, and the mixture was stirred at 0° C. for 4 hours. After 4 hours, the disappearance of the compound 2 was confirmed using TLC (hexane:ethyl acetate=1:1 (volume ratio)), and then, the mixture was stirred at room temperature for 15 hours in order to make unreacted TsCl disappear. After 15 hours, the disappearance of TsCl was confirmed by TLC, and 300 ml of ion-exchanged water and 500 ml of diethyl ether were added. The mixed solution was washed once with 500 ml of a saturated aqueous sodium bicarbonate solution and three times with 500 ml of a saturated saline solution. Activated carbon (5.0 g) and sodium sulfate were added to the organic layer, which was dried and filtered. The filtrate was concentrated under reduced pressure to obtain a reaction product containing the compound 4 as a pale yellow transparent liquid. Further, by TLC measurement and NMR measurement, it was confirmed that the above compound 3 was also contained in the obtained reaction product.

Yield: 818 g

Example 3 Synthesis of One-Terminal Trityl Group-Containing Monodispersed PEG (Compound 5) with Chain Length of 8

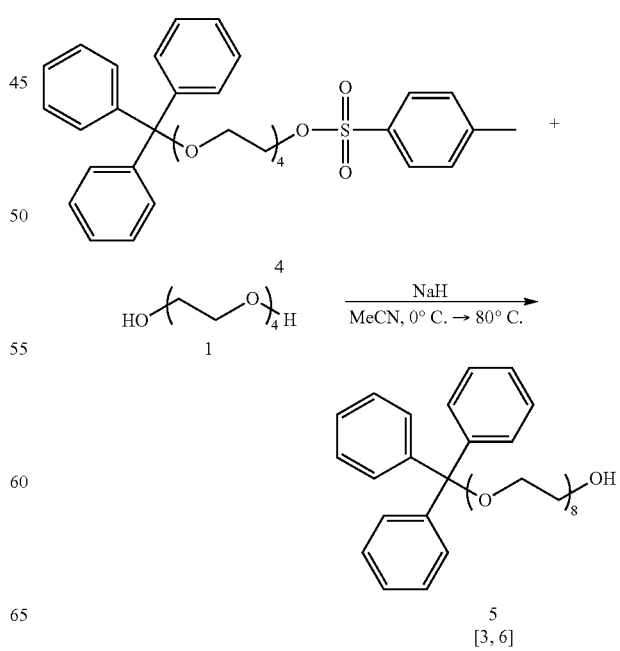

Figure 3:
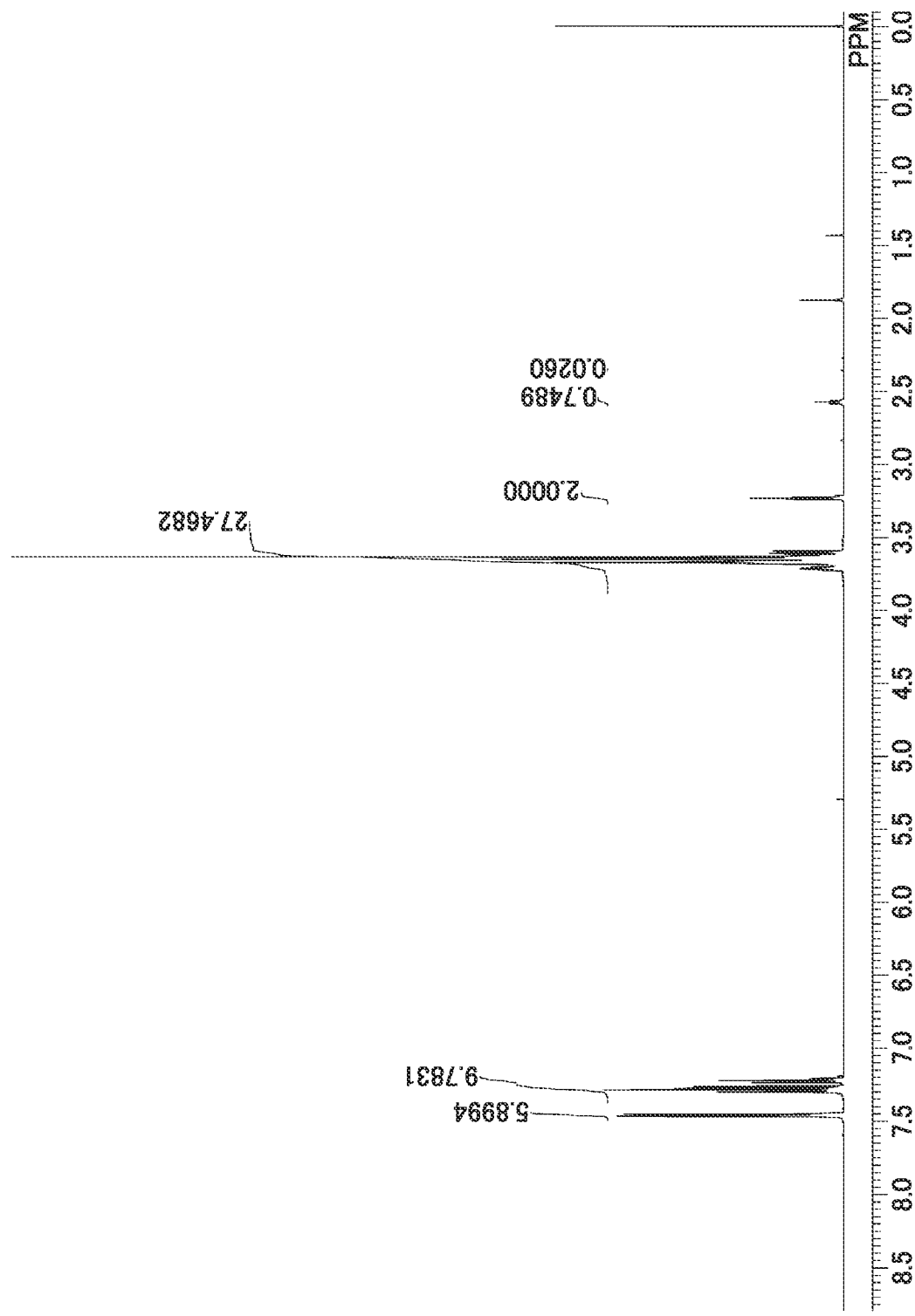
FIG. 3 shows results of NMR measurement of the compound 5 in Example 3.

Sodium hydride (81 g) was placed in a two-necked eggplant-shaped flask, and the inside was replaced with nitrogen. It was washed twice with dehydrated hexane (500 ml×2 times), 1,800 ml of THF was added, and the whole was cooled to 0° C. Tetraethylene glycol 1 (2,000 ml, 11.5 mol) azeotropically dehydrated three times with 500 ml of toluene was placed in a dropping funnel and added dropwise thereto over a period of 30 minutes. After completion of the dropwise addition, the reaction product containing the compound 4 obtained in Example 2 (compound 4: 813 g, less than 1.4 mol), which had been azeotropically dehydrated three times with 500 ml of toluene, was mixed with 1,000 ml of THF, and the resultant one was placed in the same dropping funnel and added dropwise over a period of 15 minutes. After completion of dropwise addition, the reaction mixture was heated to 40° C. and stirred for 19 hours. After 19 hours, it was confirmed that the compound 4 disappeared using TLC (ethyl acetate), and the mixture was allowed to cool to room temperature. Ion-exchanged water (2,000 ml) and a saturated saline solution (2,000 ml) were added to the reaction mixture, and the layers were separated. The aqueous layer was subjected to extraction with adding 500 ml of diethyl ether. The separated organic layers were mixed and washed once with 500 ml of a mixed solution of ion-exchanged water/a saturated saline solution (ion-exchanged water:saturated saline solution=1:1 (volume ratio)) and five times with 500 ml of a saturated saline solution. Activated carbon (5.0 g) and sodium sulfate were added to the organic layer, which was dried and filtered. The filtrate was concentrated under reduced pressure to obtain a reaction product containing the compound 5 as a pale yellow transparent liquid. Further, it was confirmed by the results of TLC measurement and NMR measurement (FIG. 3) that the above compounds 3 and 6 were also contained in the obtained reaction product.

Compound 5

$^1$H-NMR (CDCl$_3$, internal standard TMS); δ (ppm):

2.58 (1H, t, —C—(OCH$_2$CH$_2$)$_8$—O$\underline{H}$), 3.23 (2H, t, (C$_6$H$_5$)$_3$C—OC$\underline{H}_2$CH$_2$—, including those derived from compounds 3, 6), 3.45-3.85 (30H, m, —OCH$_2$C$\underline{H}_2$—(OC$\underline{H}_2$C$\underline{H}_2$)$_3$—OH, including those derived from compounds 3, 6)

7.21-7.47 (15H, m, (C$_6$$\underline{H}_5$)$_3$C—OCH$_2$CH$_2$—, including compounds 3, 6)

Yield: 788 g

Figure 4:
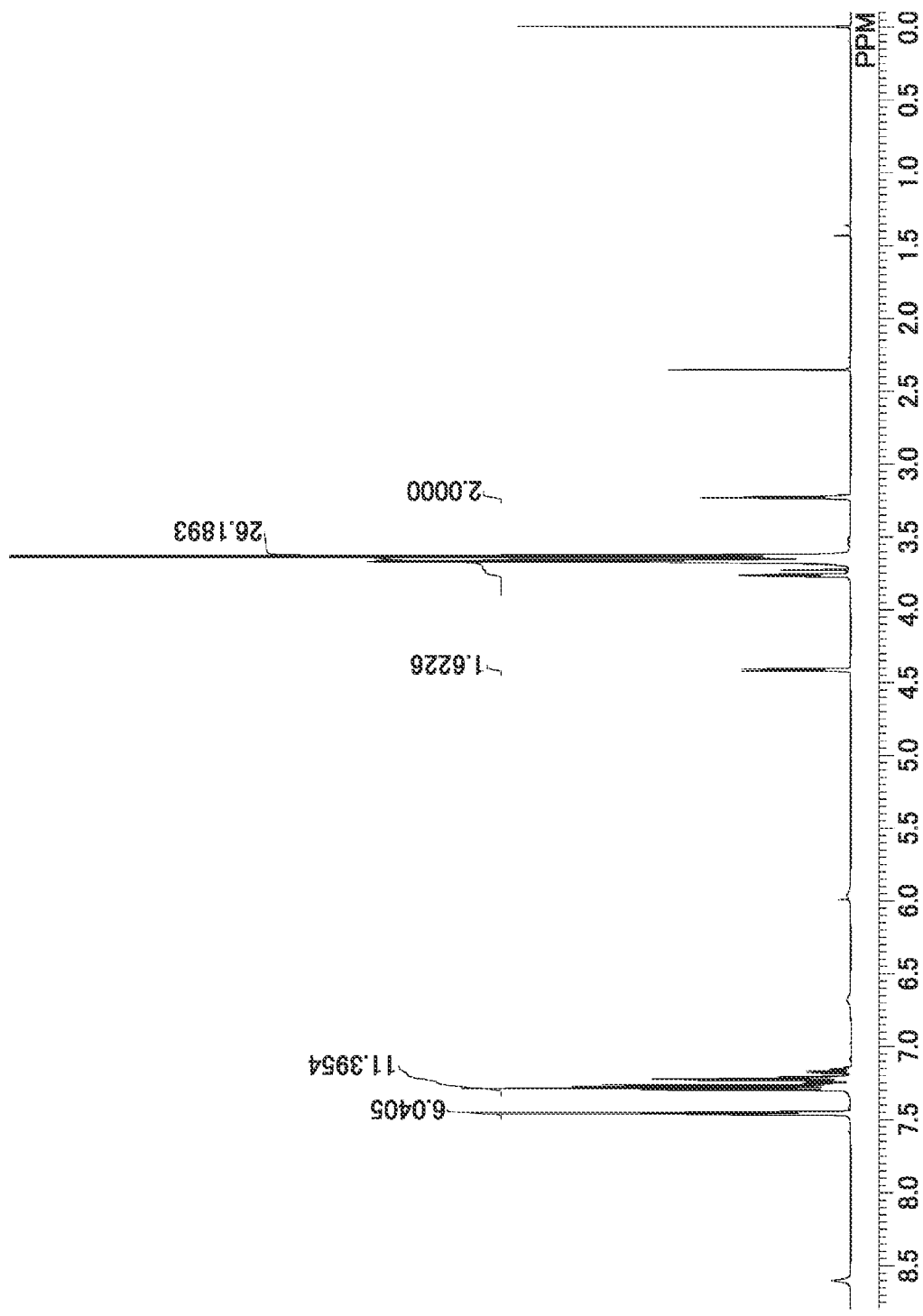
FIG. 4 shows results of NMR measurement of the compound 5' in Example 3.

From the results of $^1$H-NMR measurement (FIG. 4) of the compound 5' in which the hydroxyl group was labelled by treating the obtained reaction product containing the compound 5 using trichloroacetyl isocyanate, it was confirmed that the compounds 3 and 6 were contained in an amount of about 12 mol % (compound 3: 7 mol %, compound 6: 5 mol %, rough estimation)

Calculation Formula of Contents of Compounds 3, 6 Based on the Peak at δ 3.23:

(((2−[δ4.42])/4H)/([δ4.42]/2H))×100(mol %)

As the content of the compound 3, the numerical value in Example 1 was applied.

Compound 5'

$^1$H-NMR (CDCl$_3$, internal standard TMS); δ (ppm):

3.23 (2H, t, (C$_6$H$_5$)$_3$C—OC$\underline{H}_2$CH$_2$—, including those derived from compounds 3, 6), 3.45-3.85 (28H, m, —OCH$_2$C$\underline{H}_2$—(OC$\underline{H}_2$C$\underline{H}_2$)$_6$—OC$\underline{H}_2$CH$_2$—OCO—, including those derived from compounds 3, 6)

4.42 (2H, t, —OC$\underline{H}_2$CH—OCO—NH—COCCl$_3$b), 7.21-7.47 (15H, m, (C$_6$$\underline{H}_5$)$_3$C—OCH$_2$—, including those derived from compounds 3, 6)

Example 4 Synthesis of Compound 7

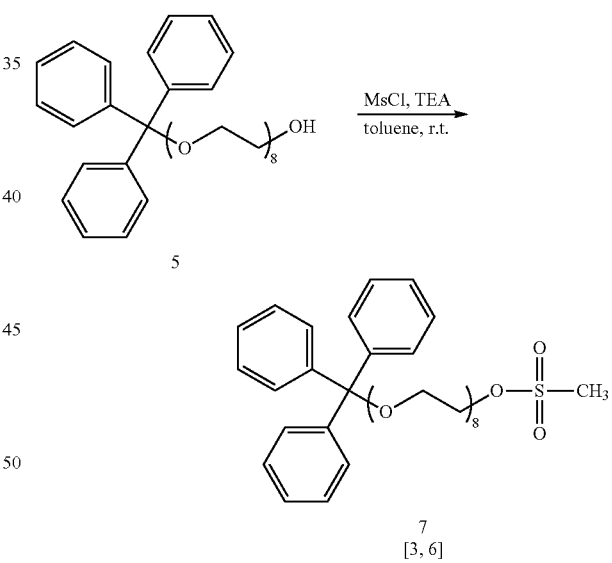

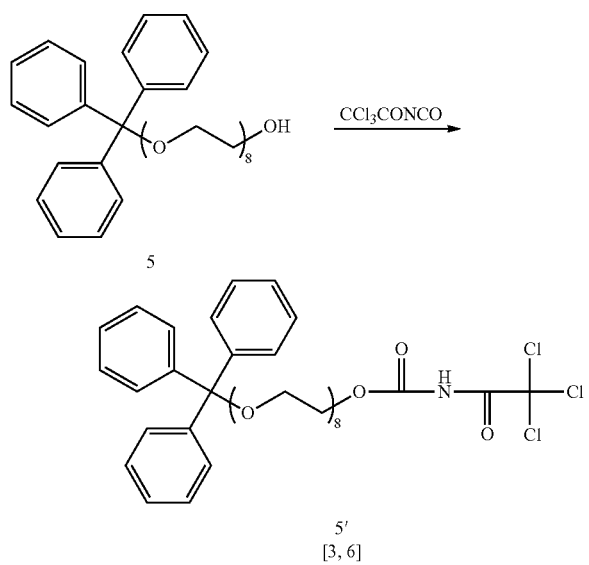

The reaction product containing the compound 5 synthesized in Example 3 (compound 5: 598 g, less than 0.83 mol) and toluene (2,450 mi) were placed in an eggplant-shaped flask, the inside of the eggplant-shaped flask was purged with nitrogen, and triethylamine (139 ml, 1.00 mol) was added. Methanesulfonyl chloride (71 ml, 0.92 mol) was added dropwise at 0° C., followed by stirring at room temperature for 2 hours. After 2 hours, the disappearance of the compound 5 was confirmed by TLC measurement, and 700 ml of 1M HCl aq. was added and the layers were separated. The organic layer was washed once with 700 ml of 1M HCl aq., twice with 700 ml of a saturated aqueous sodium bicarbonate solution, and once with 700 ml of a saturated saline solution. Sodium sulfate was added to the organic layer, which was dried and filtered. The filtrate was concentrated under reduced pressure to obtain a reaction product containing the compound 7 as a pale yellow transparent liquid. Further, it was confirmed by TLC measurement and NMR measurement that the above compounds 3 and 6 were also contained in the obtained reaction product.

Yield: 561 g

Example 5 Synthesis of One-Terminal Trityl Group-Containing Monodispersed PEG (Compound 8) with Chain Length of 12

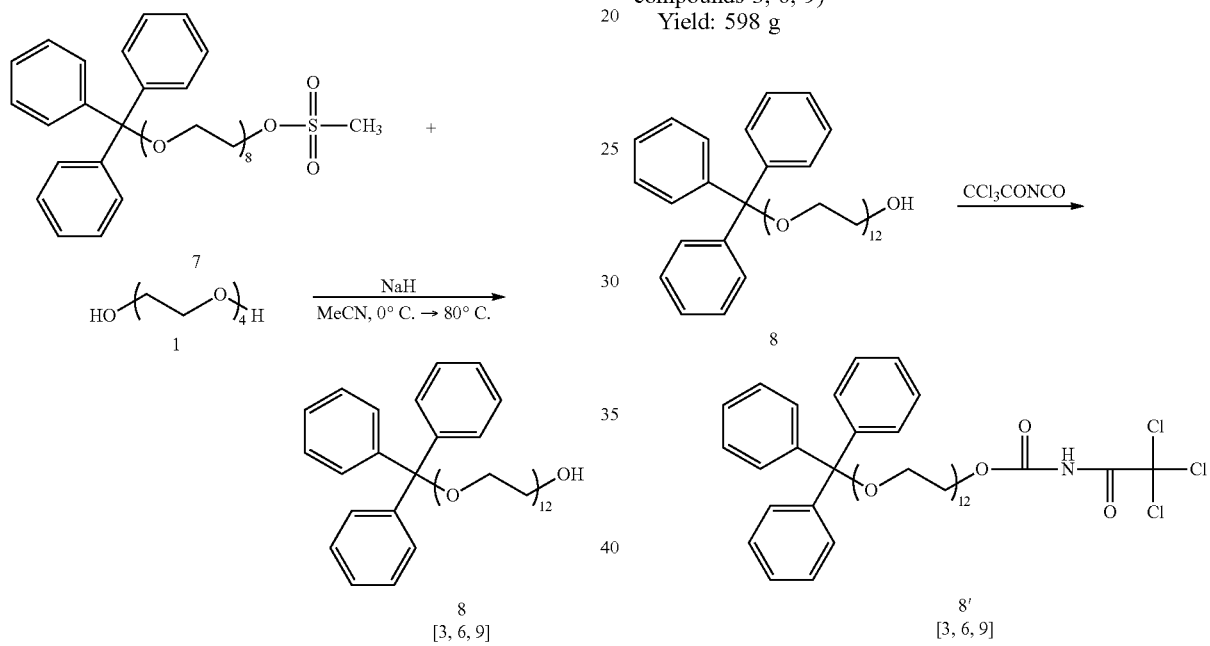

Figure 5:
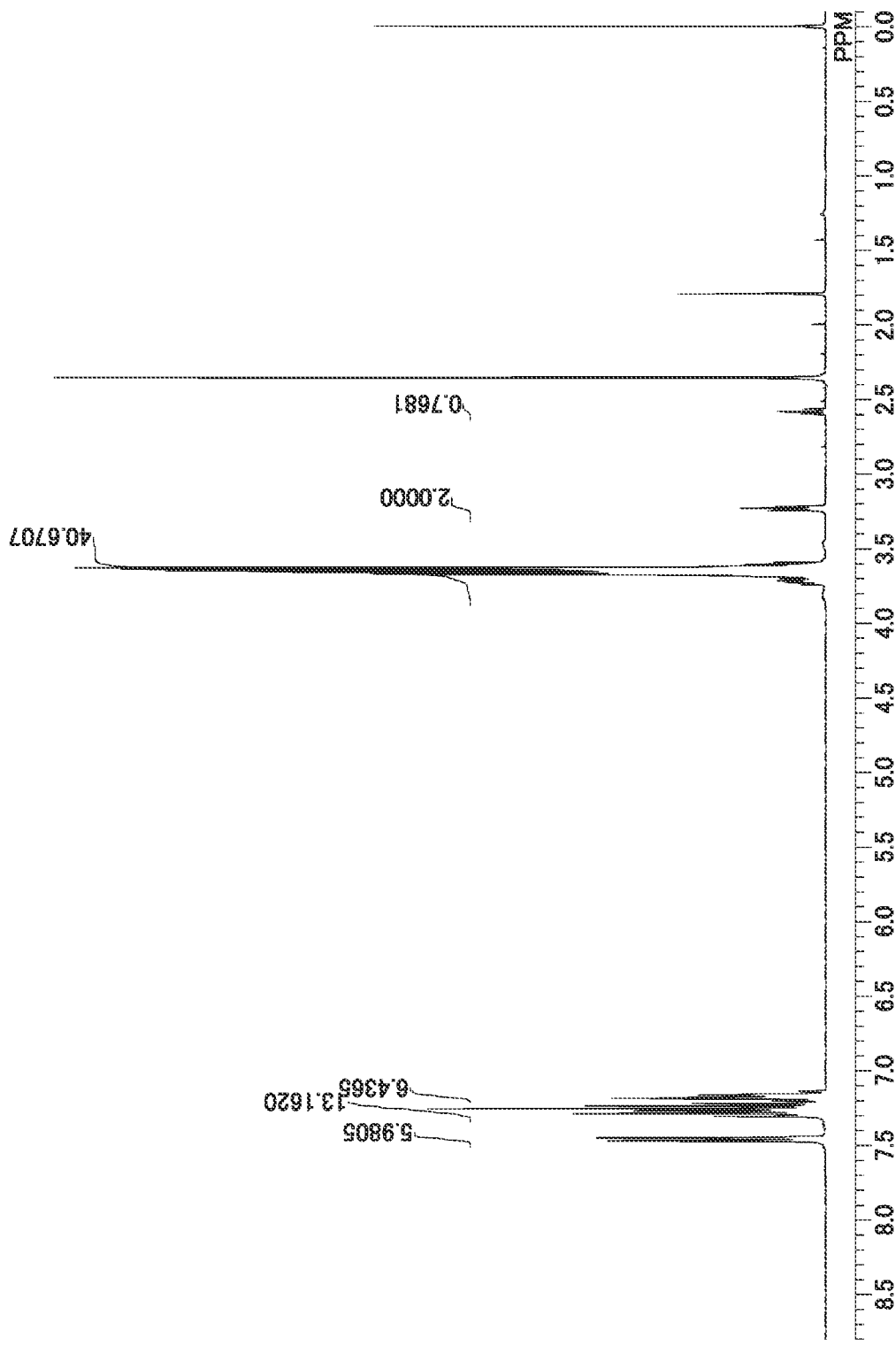
FIG. 5 shows results of NMR measurement of the compound 8 in Example 5.

Sodium hydride (46 g) was placed in a two-necked eggplant-shaped flask, and the inside was replaced with nitrogen. It was washed twice with dehydrated hexane (350 ml×2 times), 1,400 ml of MeCN was added, and the whole was cooled to 0° C. Tetraethylene glycol 1 (1,120 ml, 6.5 mol) azeotropically dehydrated three times with 2,450 ml of toluene was mixed with 350 ml of MeCN and the resultant one was placed in a dropping funnel and added dropwise over a period of 30 minutes. After completion of the dropwise addition, the reaction product containing the compound 7 obtained in Example 4 (compound 7: 561 g, less than 0.81 mol), which had been azeotropically dehydrated three times with 350 ml of toluene, was mixed with 350 ml of MeCN, and the resultant one was placed in the same dropping funnel and added dropwise over a period of 15 minutes. After completion of dropwise addition, the reaction mixture was heated to 80° C. and stirred for 3 hours. After 3 hours, it was confirmed by $^1$H NMR (CDCl$_3$) that the compound 7 disappeared, and the mixture was allowed to cool to room temperature. The reaction mixture was concentrated under reduced pressure, and 1,400 ml of toluene was added to the residue. This toluene solution was washed twice with 700 ml of a saturated aqueous ammonium chloride solution and three times with 700 ml of a saturated saline solution. Sodium sulfate was added to the organic layer, which was dried and filtered. The filtrate was concentrated under reduced pressure to obtain a reaction product containing the compound 8 as a pale yellow transparent liquid. Further, it was confirmed by the results of TLC measurement and NMR measurement (FIG. 5) that the above compounds 3, 6 and 9 were also contained in the obtained reaction product.

Compound 8

$^1$H-NMR (CDCl$_3$, internal standard, TMS); δ (ppm):
2.57 (H, b, —C—(OCH$_2$CH$_2$)$_{12}$—O$\underline{H}$,
3.23 (2H, t, (C$_6$H$_5$)$_3$C—OC$\underline{H}_2$CH$_2$—, including those derived from compounds 3, 6, 9),
3.45-3.85 (46H, m, —OCH$_2$C$\underline{H}_2$—(OC$\underline{H}_2$C$\underline{H}_2$)$_{11}$—OH, including those derived from compounds 3, 6, 9)
7.21-7.47 (15H, m, (C$_6$$\underline{H}_5$)$_3$C—OCH$_2$CH$_2$—, including compounds 3, 6, 9)

Yield: 598 g

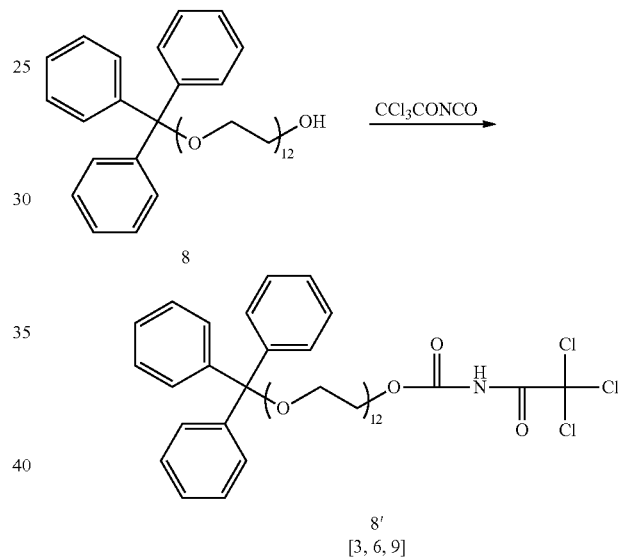

Figure 6:
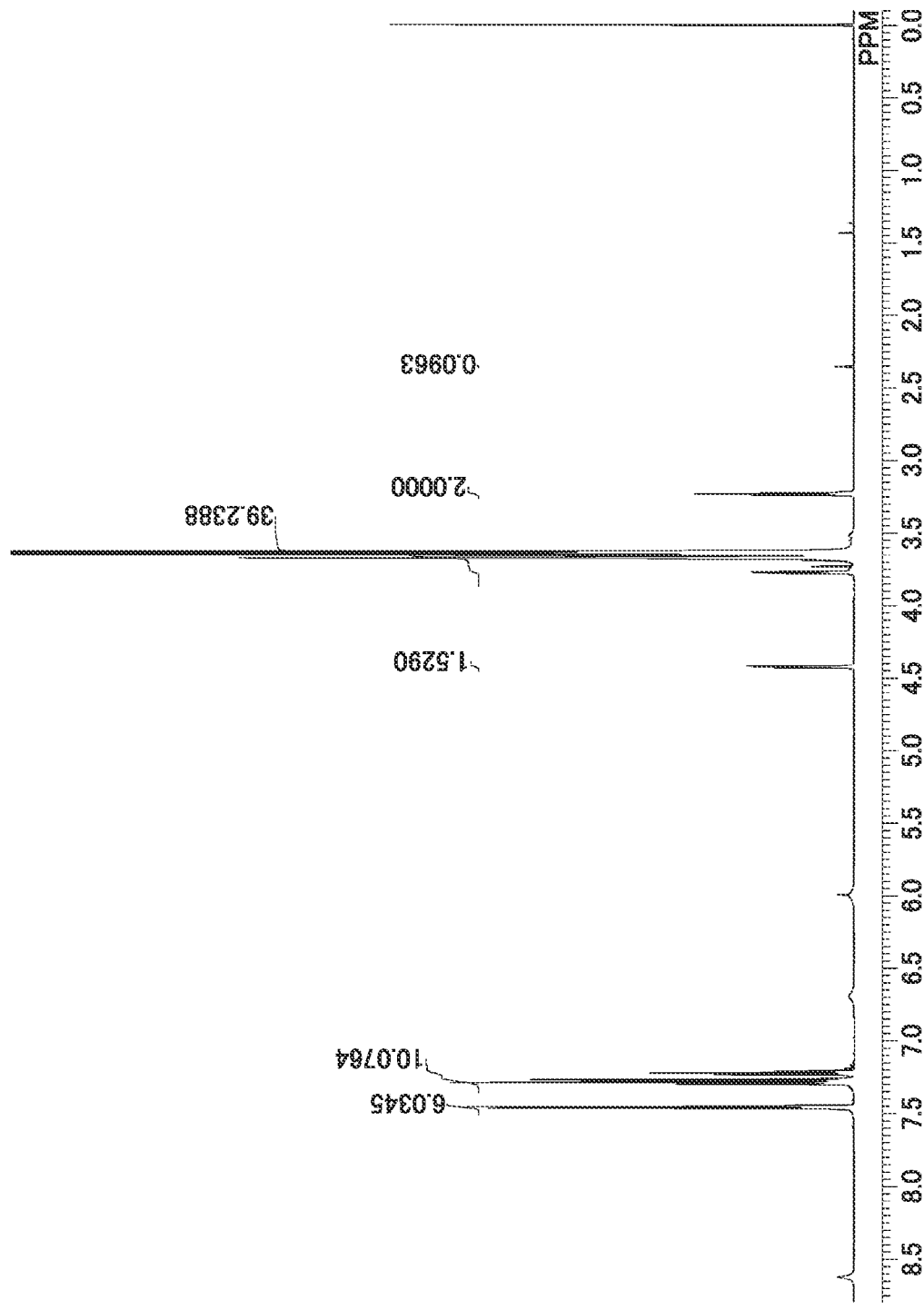
FIG. 6 shows results of NMR measurement of the compound 8' in Example 5.

From the results of $^1$H-NMR measurement (FIG. 6) of the compound 8 in which the hydroxyl group was labelled by treating the obtained reaction product containing the compound 8 using trichloroacetyl isocyanate, it was confirmed that the compounds 3, 6 and 9 were contained in an amount of about 15 mol % (compound 3: 7 mol %, compound 6: 5 mol %, compound 9: 3 mol %, rough estimation)

Calculation formula of contents of compounds 3, 6, 9 based on the peak at δ 3.23:

$$(((2-[\delta 4.42])/4H)/([\delta 4.42]/2H))\times 100 \text{(mol \%)}$$

As the contents of the compounds 3, 6, the numerical values in Examples 1 and 3 were applied.

Compound 8'

$^1$H-NMR (CDCl$_3$, internal standard TMS); δ (ppm):
3.23 (2H, t, (C$_6$H$_5$)C—OC$\underline{H}_2$CH$_2$—, including those derived from compounds 3, 6, 9), 3.45-3.85 (44H, m, —OCH$_2$C$\underline{H}_2$—(OC$\underline{H}_2$C$\underline{H}_2$)$_{11}$—OCH$_2$CH$_2$—OCO—, including those derived from compounds 3, 6, 9)
4.42 (2H, t, —OC$\underline{H}_2$CH—OCO—NH—COCCl$_3$),
7.21-7.47 (151, m, (C$_6$$\underline{H}_5$)$_3$C—OCH$_2$CH$_2$—, including those derived from compounds 3, 6, 9)

Example 6 Purification of One-Terminal Trityl Group-Containing Monodispersed PEG (Compound 5) with Chain Length of 8

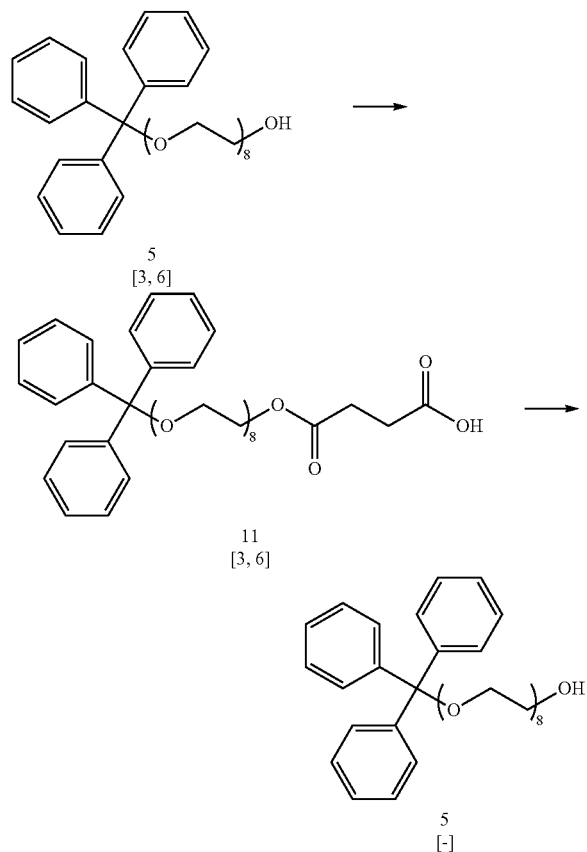

Step (A)

A mixture containing the compound 5 as a main component (38 g, 62 mmol, including about 12 mol %, about 17% by mass of compounds 3, 6 in total from Example 3), sodium acetate (3 g, 37 mmol), and toluene (38 g) were added to a four-necked flask fitted with a cooling tube, a thermometer, and a nitrogen-inlet tube. The inside of the flask was purged with nitrogen, and succinic anhydride (7 g, 68 mmol) was added. The mixture was stirred at 70° C. for 1 hour. After 1 hour, the disappearance of the compound 5 was confirmed by TLC measurement, and the whole was cooled to 40° C. or lower. After adding toluene (61 g), a 23.4 wt % saline solution (228 g) was added, and liquid-separation washing was performed at 55° C. three times in total.

Step (B)

Hexane (38 g), methanol (61 g) and a citrate phosphate (0.2 M) buffer of pH 5.5 (60.8 g) were charged into the organic layer to separate layers. It was confirmed that the pH of the cloudy aqueous layer was from 6 to 7, and the mixture was stirred at 45 to 50° C. for 15 minutes and then allowed to stand. The transparency of the upper and lower layers was confirmed, and the organic layer was discarded. Toluene (99 g) and hexane (38 g) were added to the aqueous layer, and the mixture was stirred at 45 to 50° C. for 15 minutes and then allowed to stand. After separation into upper and lower layers, the organic layer was discarded. After liquid-separation washing was performed twice more with adding toluene (99 g) and hexane (38 g), it was confirmed from TLC measurement that the spots derived from the ditritylated impurities (3, 6, 9) disappeared.

Solvent Mass Ratio at the Time of Liquid-Separation Washing:

Organic solvent I:Organic solvent II:Organic solvent III=30.8%:50.0%:19.2%

Step (C)

After washing, a 400 g/L aqueous sodium hydroxide solution (11 g) was added to the aqueous layer (pH 6.3), and the mixture was stirred at 25° C. for 2 hours. From the TLC measurement of the aqueous layer (pH 12.8) after 2 hours, the disappearance of the compound 11 was confirmed.

Figure 7:
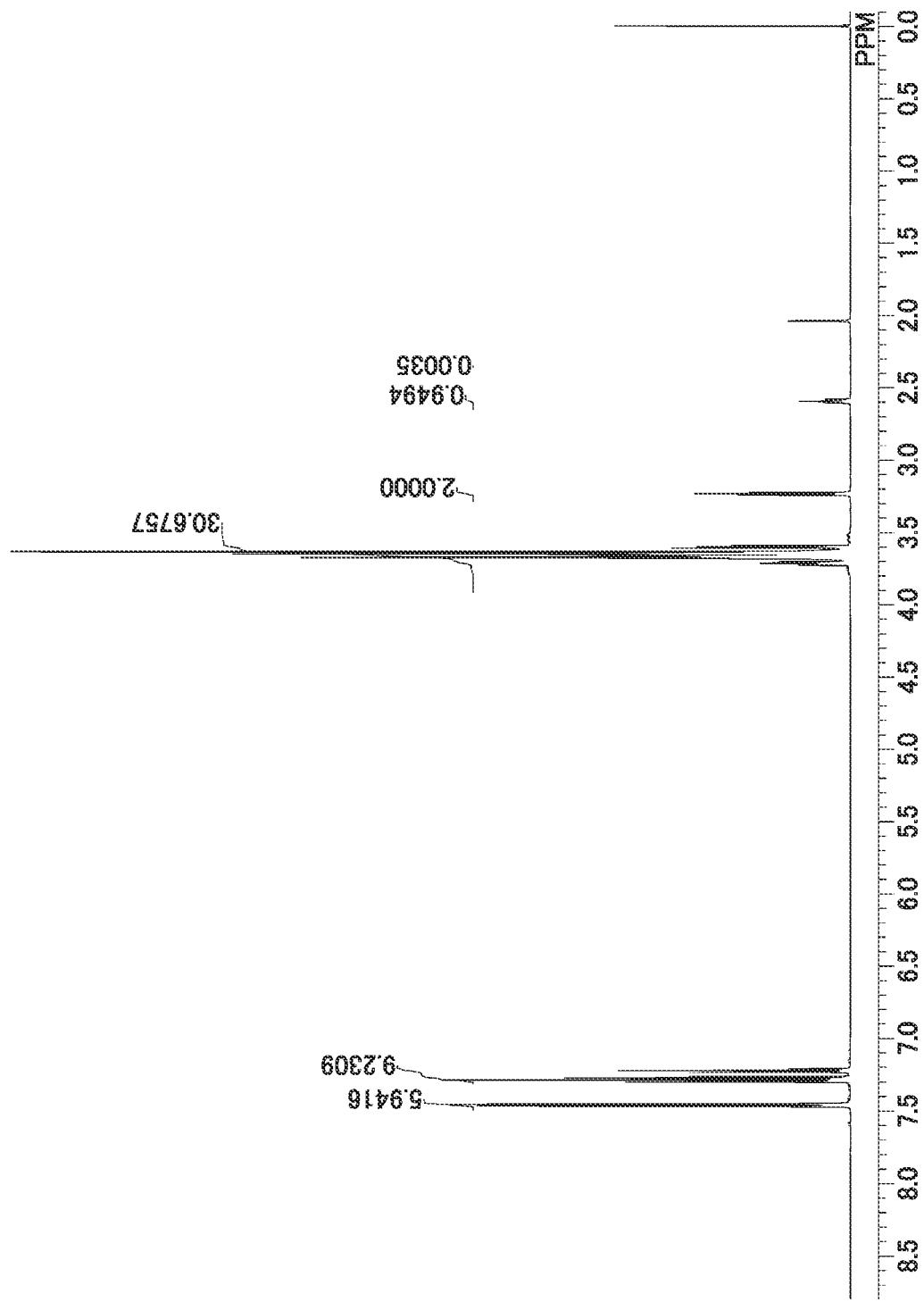
FIG. 7 shows results of NMR measurement of the compound 5 after purification in Example 6.
Figure 8:
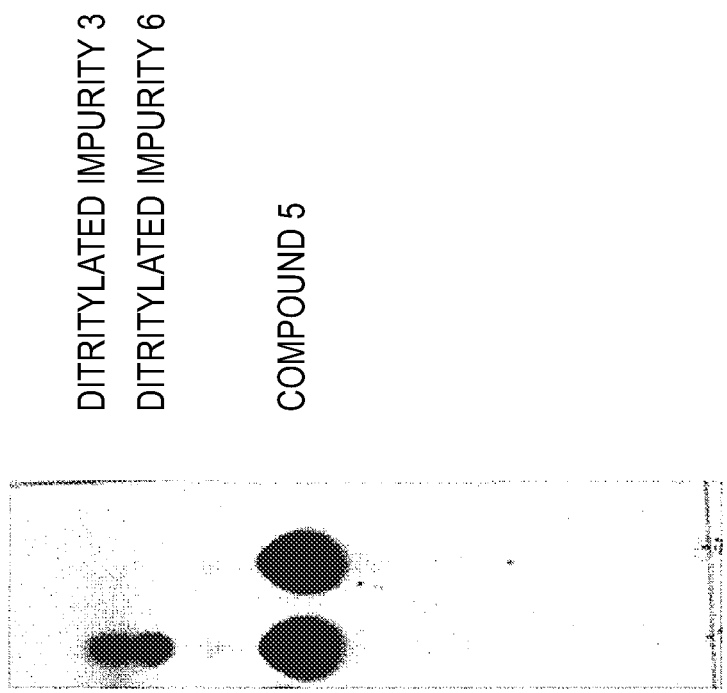
FIG. 8 shows a TLC chart of the compound 5 before and after purification in Example 6, the left showing before purification and the right showing after purification.

Toluene (331 g) was added to the aqueous layer, and the mixture was stirred at 30° C. for 15 minutes. After the mixture was allowed to stand and layer separation was confirmed, it was confirmed from TLC measurement that the compound 5 did not remain in the aqueous layer, and the aqueous layer was discarded. A 20 wt % saline solution (228 g) was added to the organic layer, and liquid-separation washing was performed at 30° C. The collected organic layer was dehydrated with sodium sulfate (38 g), filtered using toluene, and then concentrated to obtain the compound 5 (21 g). The integrated values of the results of NMR measurement (FIG. 7) were in agreement with the theoretical values, and from the comparison of the TLC results of the compound 5 before and after purification (FIG. 8), it was confirmed that no ditritylated impurity was contained.

Ditritylated impurities 3, 6 N.D. (TLC measurement, see FIG. 8) yield 21 g, yield 67%

Compound 5 (after Purification)

$^1$H-NMR (CDCl$_3$, internal standard TMS); δ (ppm):
2.52 (1H, s, —C—(OCH$_2$CH$_2$)$_8$—O$\underline{H}$)
3.23 (2H, t, (C$_6$H$_5$)$_3$C—OC$\underline{H_2}$—),
3.45-3.85 (30H, m, —OCH$_2$C$\underline{H_2}$—(OC$\underline{H_2}$C$\underline{H_2}$)$_7$—OH),
7.21-7.47 (15H, m, (C$_6$H$_5$)$_3$C—O—CH$_2$—)

Example 7 Purification of One-Terminal Trityl Group-Containing Monodispersed PEG (Compound 8) with Chain Length of 12

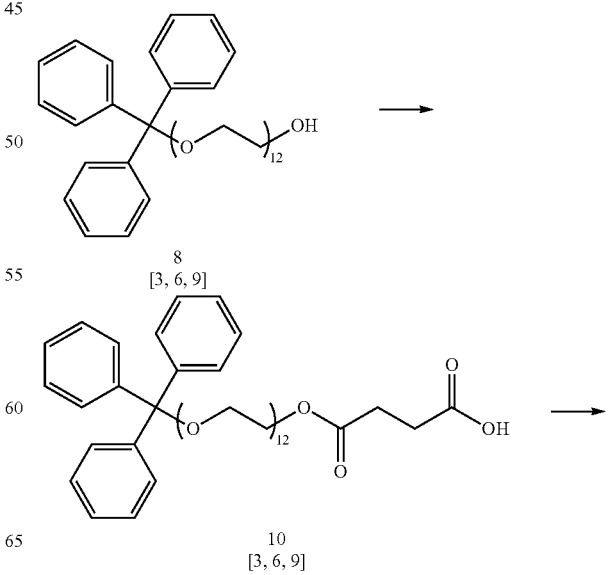

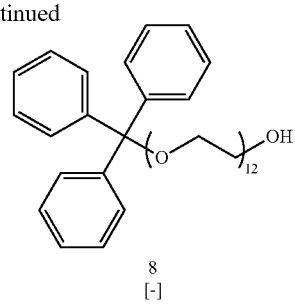

8
[-]

Step (A)

A mixture containing the compound 8 as a main component (145 g, compound 8: 184 mmol, including about 15 mol %, about 18% by mass of compounds 3, 6, 9 in total from Example 5), sodium acetate (9 g, 110 mmol), and toluene (145 g) were added to a four-necked flask fitted with a cooling tube, a thermometer, and a nitrogen-inlet tube. The inside of the flask was purged with nitrogen, and succinic anhydride (20 g, 202 mmol) was added. The mixture was stirred at 70° C. for 1 hour. After 1 hour, the disappearance of the compound 8 was confirmed by TLC measurement, and the whole was cooled to 40° C. or lower. After adding toluene (232 g), a 23.4 wt % saline solution (870 g) was added, and liquid-separation washing was performed at 55° C. three times in total.

Step (B)

Figure 9:
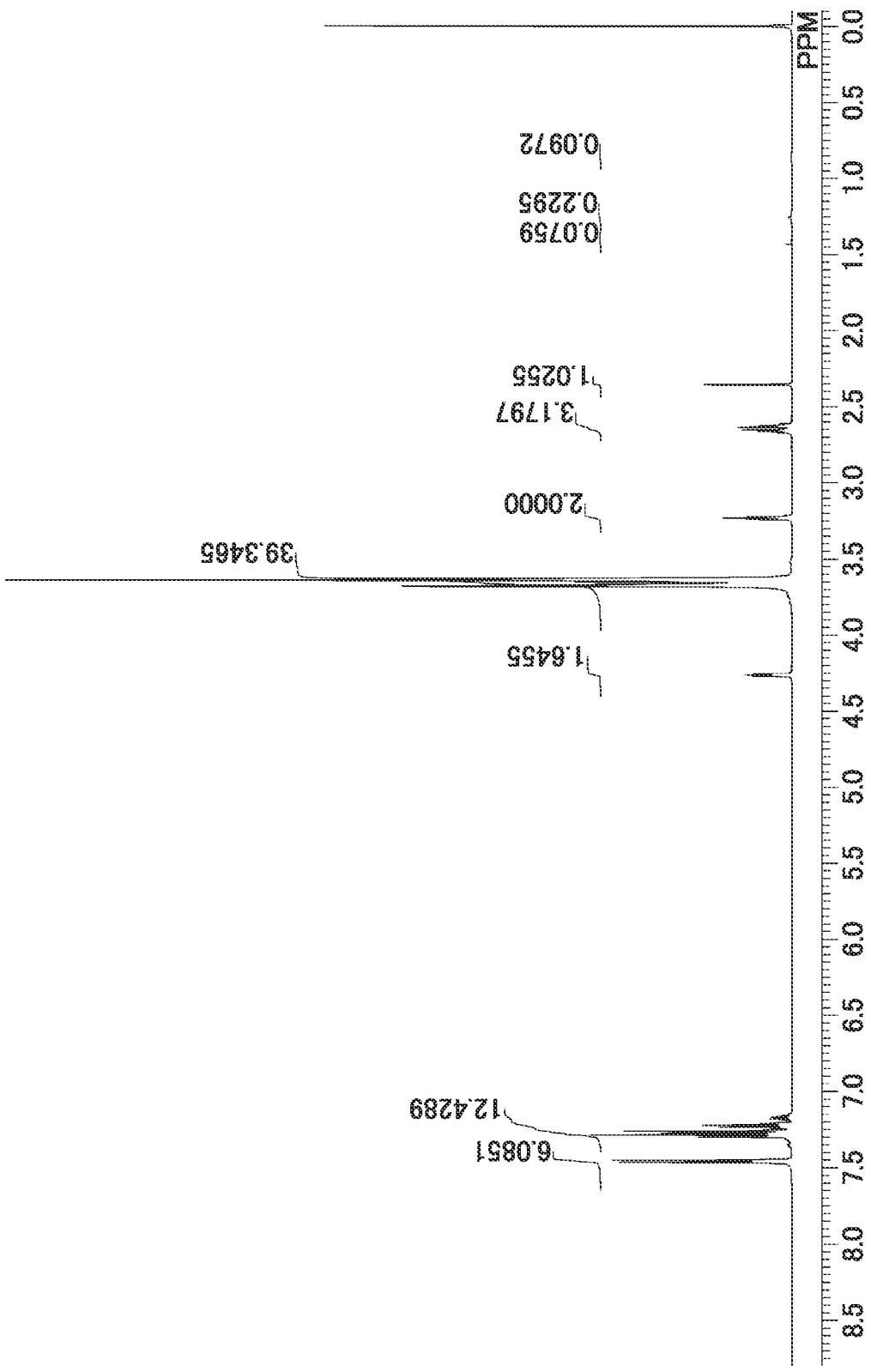
FIG. 9 shows results of NMR measurement of the compound 10 before liquid-separation washing (after completion of step A) in Example 7.
Figure 10:
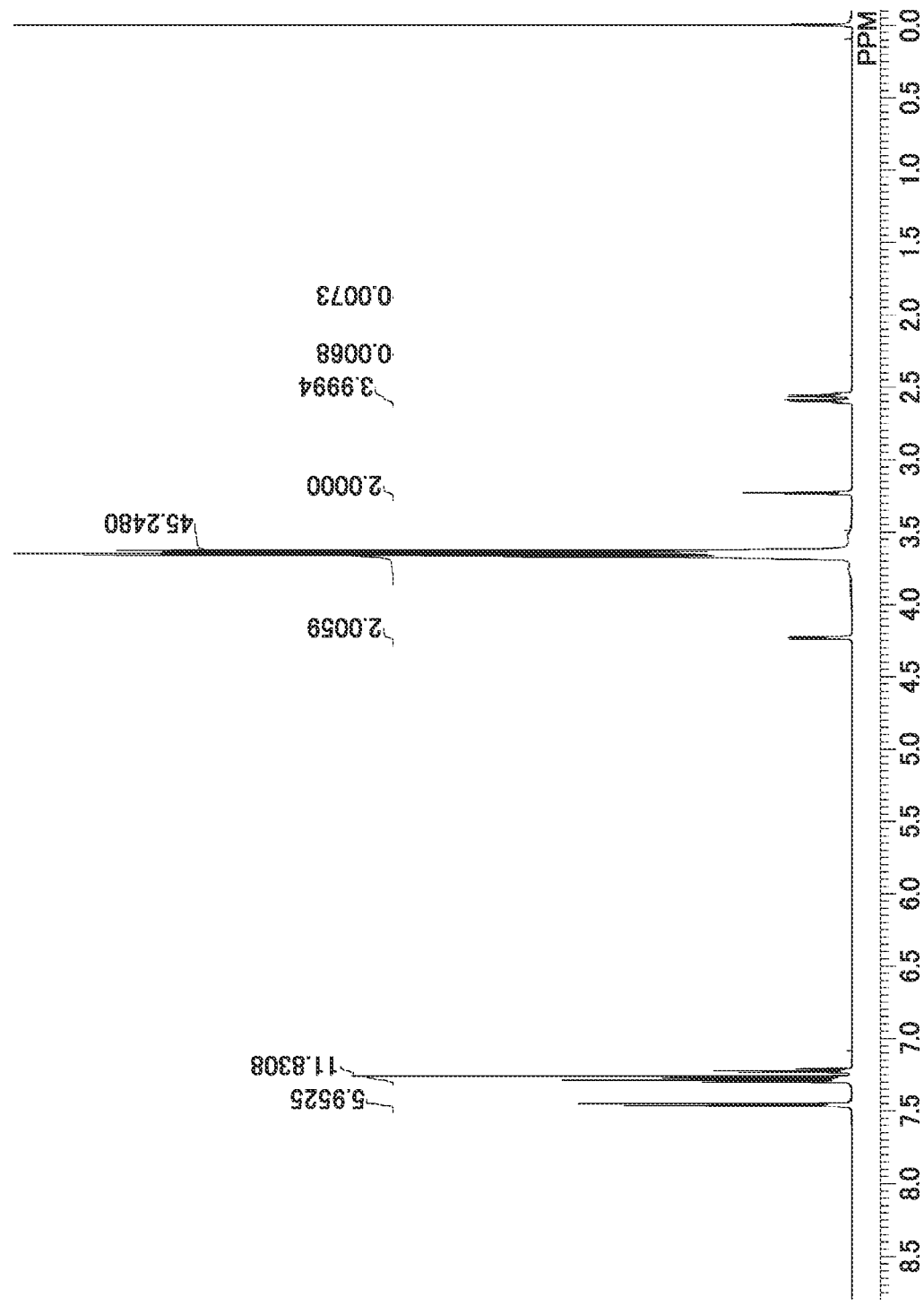
FIG. 10 shows results of NMR measurement of the compound 10 after liquid-separation washing (after completion of step B) in Example 7.

Hexane (145 g), methanol (232 g) and a citrate phosphate (0.2 M) buffer of pH 5.5 (232 g) were charged into the organic layer to separate layers. It was confirmed that the pH of the cloudy aqueous layer was from 5 to 6, and the mixture was stirred at 45 to 50° C. for 15 minutes and then allowed to stand. The transparency of the upper and lower layers was confirmed, and the organic layer was discarded. Toluene (378 g) and hexane (145 g) were added to the aqueous layer, and the mixture was stirred at 45 to 50° C. for 15 minutes and then allowed to stand. After separation into upper and lower layers, the organic layer was discarded. After liquid-separation washing was performed twice more with adding toluene (378 g) and hexane (145 g), it was confirmed from TLC measurement that the spots derived from the ditritylated impurities (3, 6, 9) disappeared and the results of NMR measurement after the liquid-separation washing were in agreement with the theoretical values (before washing: FIG. 9, after washing: FIG. 10).

Compound 10 (after Purification)

$^1$H-NMR (CDCl$_3$, internal standard TMS); δ (ppm):

2.62 (4H, m, —OCO—C$\underline{H}_2$C$\underline{H}_2$—COOH)

3.23 (2H, t, (C$_6$H$_5$)$_3$C—OC$\underline{H}_2$—), 3.45-3.85 (44H, m, —OCH$_2$C$\underline{H}_2$—(OC$\underline{H}_2$C$\underline{H}_2$)$_{10}$—OCH$_2$C$\underline{H}_2$—O—CO—), 4.25 (2H, t, —OCH$_2$C$\underline{H}_2$—OCO—CH$_2$CH$_2$—), 7.21-7.47 (15H, m, (C$_6$$\underline{H}_5$)$_3$C—O—CH$_2$—)

Solvent Mass Ratio at the Time of Liquid-Separation Washing:

Organic solvent I:Organic solvent II:Organic solvent III=30.7%:50.1%:19.2%

Step (C)

After washing, a 4001 g/L aqueous sodium hydroxide solution (32 g) was added to the aqueous layer (pH 6.0), and the mixture was stirred at 25° C. for 2 hours. From the TLC measurement of the aqueous layer (pH 13) after 2 hours, the disappearance of the compound 10 was confirmed.

Figure 11:
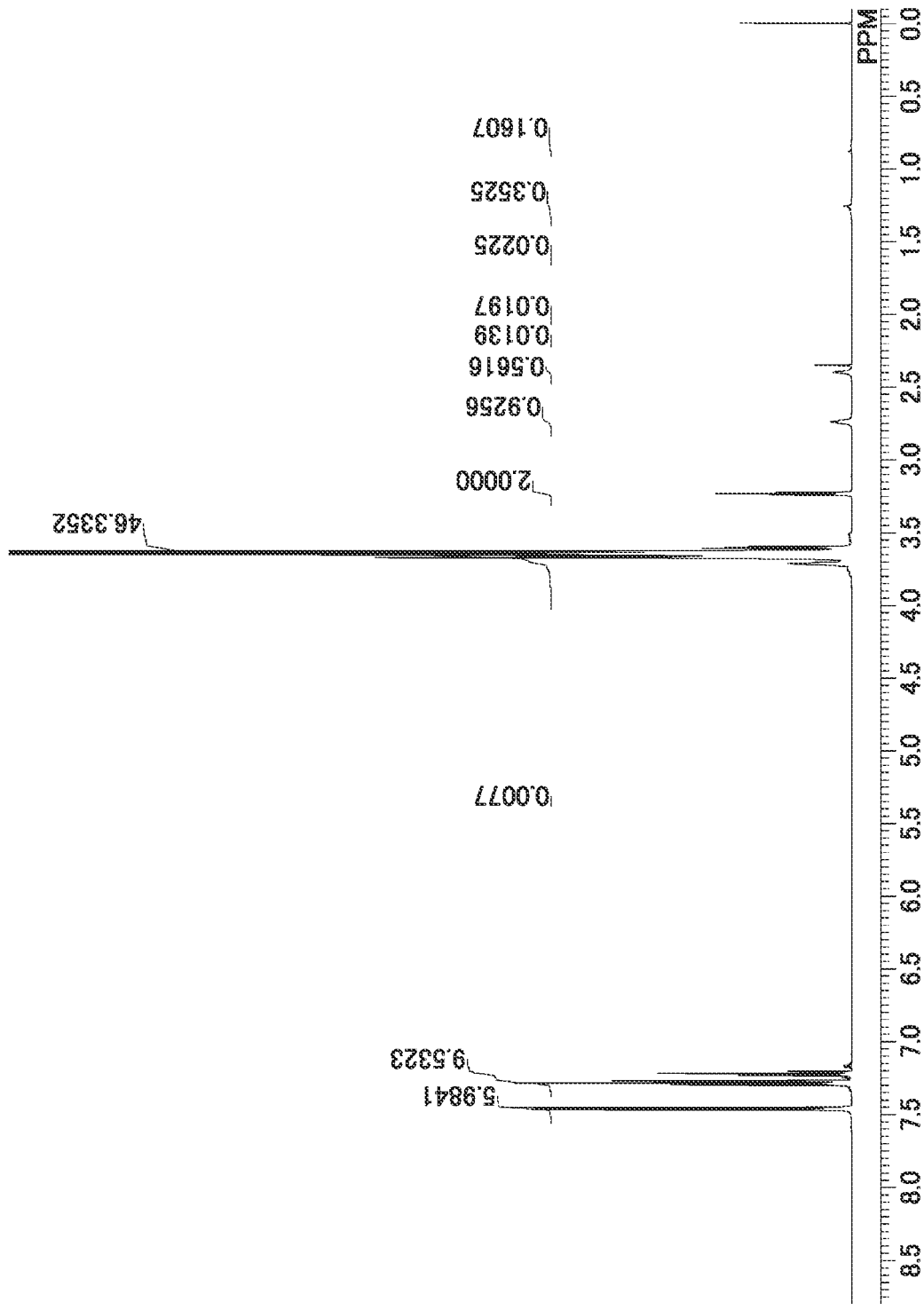
FIG. 11 shows results of NMR measurement of the compound 8 after purification (after completion of step C) in Example 7.
Figure 12:
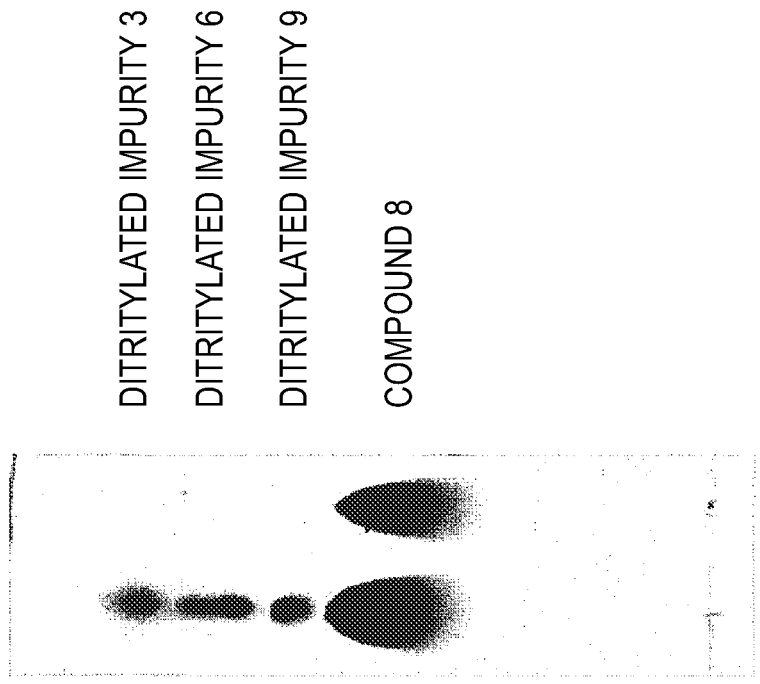
FIG. 12 shows a TLC chart of the compound 8 before and after purification in Example 7, the left showing before purification and the right showing after purification.

Toluene (1,260 g) was added to the aqueous layer, and the mixture was stirred at 30° C. for 15 minutes. After the mixture was allowed to stand and layer separation was confirmed, it was confirmed from TLC measurement that the compound 8 did not remain in the aqueous layer, and the aqueous layer was discarded. A 20 wt % saline solution (870 g) was added to the organic layer, and liquid-separation washing was performed at 30° C. The collected organic layer was dehydrated with sodium sulfate (145 g), filtered using toluene, and then concentrated to obtain the compound 8 (98 g). The integrated values of the results of NMR measurement (FIG. 11) were in agreement with the theoretical values, and from the comparison of the TLC results of the compound 8 before and after purification (FIG. 12), it was confirmed that no ditritylated impurity was contained.

Ditritylated impurities 3, 6, 9 N.D. (TLC measurement, see FIG. 12), yield 98 g, yield 82%

Compound 8 (after Purification)

$^1$H-NMR (CDCl$_3$, internal standard TMS); δ (ppm):

2.57 (1H, s, —OCH$_2$CH$_2$—(OCH$_2$CH$_2$)$_{11}$—O$\underline{H}$)

3.23 (2H, t, (C$_6$H$_5$)$_3$C—OC$\underline{H}_2$CH$_2$—), 3.45-3.85 (46H, m, —OCH$_2$C$\underline{H}_2$—(OC$\underline{H}_2$C$\underline{H}_2$)$_{11}$—OH), 7.21-7.47 (15H, m, (C$_6$$\underline{H}_5$)$_3$C—O—CH$_2$CH$_2$—)

Example 8 Purification of One-Terminal Trityl Group-Containing Monodispersed PEG with Chain Length of 12, Use of Glutaric Anhydride

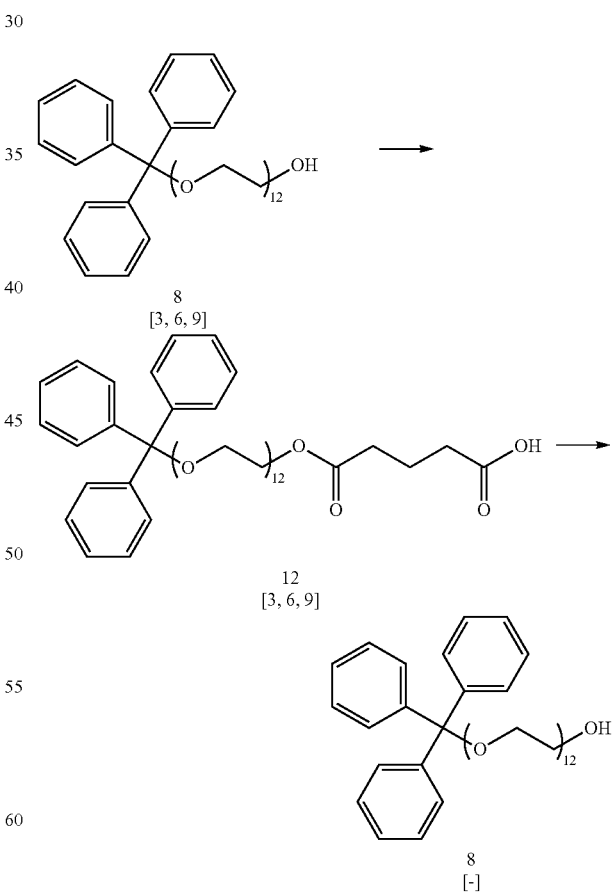

Step (A)

A mixture containing the compound 8 as a main component (30 g, 38 mmol, including about 15 mol %, about 18% by mass of compounds 3, 6, 9 in total from Example 5), sodium acetate (1.9 g, 23 mmol), and toluene (30 g) were added to a four-necked flask fitted with a cooling tube, a thermometer, and a nitrogen-inlet tube. The inside of the flask was purged with nitrogen, and glutaric anhydride (4.8 g, 42 mmol) was added. The mixture was stirred at 70° C. for 1 hour. After 1 hour, the disappearance of the compound 8 was confirmed by TLC measurement, and the whole was cooled to 40° C. or lower. After adding toluene (48 g), a 23.4 wt % saline solution (228 g) was added, and liquid-separation washing was performed at 55° C. three times in total.

Step (B)

Hexane (30 g), methanol (48 g) and a citrate phosphate (0.2 M) buffer of pH 5.5 (48 g) were charged into the organic layer to separate layers. It was confirmed that the pH of the cloudy aqueous layer was from 5 to 6, and the mixture was stirred at 45 to 50° C. for 15 minutes and then allowed to stand. The transparency of the upper and lower layers was confirmed, and the organic layer was discarded. Toluene (78 g) and hexane (30 g) were added to the aqueous layer, and the mixture was stirred at 45 to 50° C. for 15 minutes and then allowed to stand. After separation into upper and lower layers, the organic layer was discarded. After liquid-separation washing was performed three times more, it was confirmed from TLC measurement that the spots derived from the ditritylated impurities (3, 6, 9) disappeared.

Solvent Mass Ratio at the Time of Liquid-Separation Washing:

Organic solvent I:Organic solvent II:Organic solvent III=30.8%:50.0%:19.2%

Step (C)

After washing, a 400 g/L aqueous sodium hydroxide solution (6.6 g) was added to the aqueous layer (pH 6.12), and the mixture was stirred at 25° C. for 4 hours. From the TLC measurement of the aqueous layer (pH 13.5) after 4 hours, the disappearance of the compound 12 was confirmed.

Toluene (261 g) was added to the aqueous layer, and the mixture was stirred at 30° C. for 15 minutes. After the mixture was allowed to stand and layer separation was confirmed, it was confirmed from TLC measurement that the compound 8 did not remain in the aqueous layer, and the aqueous layer was discarded. A 20 wt % saline solution (870 g) was added to the organic layer, and liquid-separation washing was performed at 30° C. The collected organic layer was dehydrated with sodium sulfate (30 g), filtered using toluene, and then concentrated to obtain the compound 8 (15 g). The integrated values of the results of NMR measurement were in agreement with the theoretical values, and from the comparison of the TLC results of the compound 8 before and after purification, it was confirmed that no ditritylated impurity was contained.

Ditritylated impurities N.D., yield 15 g, yield 62%

Example 9 Example with a High Organic Solvent III Ratio in Example 7

The same operations as the step (A) of Example 7 were carried out, and the solvent was added so that the solvent ratio in the step (B) became methanol (231 g), a citrate phosphate (0.2M) buffer of pH 5.5 (222 g), toluene (378 g), and hexane (290 g). Liquid-separation washing was performed at this solvent ratio, and then the liquid-separation washing operation was repeated 9 times with adding toluene (378 g) and hexane (290 g). From TLC measurement, it was confirmed that the spots derived from the ditritylated impurities (3, 6, 9) disappeared.

Solvent Mass Ratio at the Time of Liquid-Separation Washing:

Organic solvent I:Organic solvent II:Organic solvent III=25.7%:42.0%:32.3%

In the step (C), the same operations as in Example 7 were carried out to obtain the compound 8 (76 g). The integrated values of the results of NMR measurement were in agreement with the theoretical values, and it was confirmed from the comparison of TLC results of the compound 8 before and after purification that no ditritylated impurity was contained.

Ditritylated impurities N.D., yield 76 g, yield 64%

Example 10 Synthesis of Compound 13

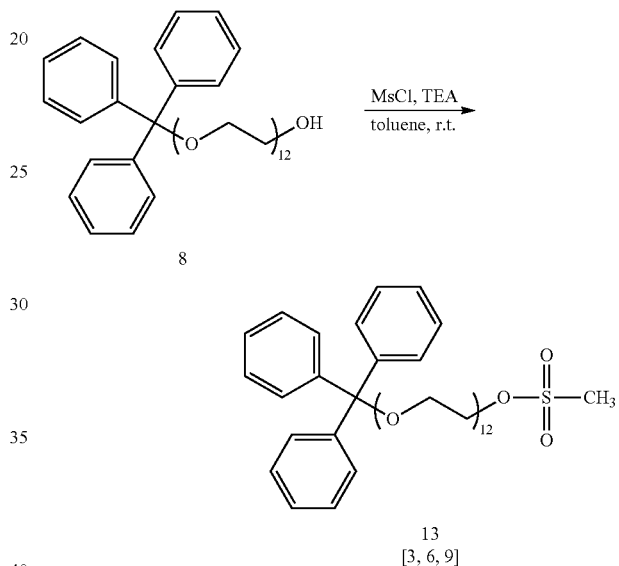

A reaction product containing the compound 8 synthesized by the method described in Example 3 (compound 8: 90 g, less than 0.11 mol) and toluene (451 ml) were placed in a four-necked flask fitted with a cooling tube, a thermometer, and a nitrogen-inlet tube. The inside of the flask was purged with nitrogen, and triethylamine (29 ml, 0.21 mol) was added. Methanesulfonyl chloride (14 ml, 0.18 mol) was added dropwise at 0° C., and the mixture was stirred at room temperature for 2 hours. After 2 hours, the disappearance of the compound 8 was confirmed by TLC measurement, and 450 ml of a 5% aqueous sodium dihydrogen phosphate solution was added and the layers were separated. The organic layer was washed once with 450 ml of a 5% aqueous sodium dihydrogen phosphate solution, twice with 450 ml of a saturated aqueous sodium bicarbonate solution, and once with 450 ml of a saturated saline solution. Sodium sulfate was added to the organic layer, which was dried and filtered. The filtrate was concentrated under reduced pressure to obtain a reaction product containing the compound 13 as a pale yellow transparent liquid. Further, it was confirmed by TLC measurement and NMR measurement that the above compounds 3, 6 and 9 were also contained in the obtained reaction product.

Yield: 96 g

Example 11 Synthesis of One-Terminal Trityl Group-Containing Monodispersed PEG (Compound 14) with Chain Length of 16

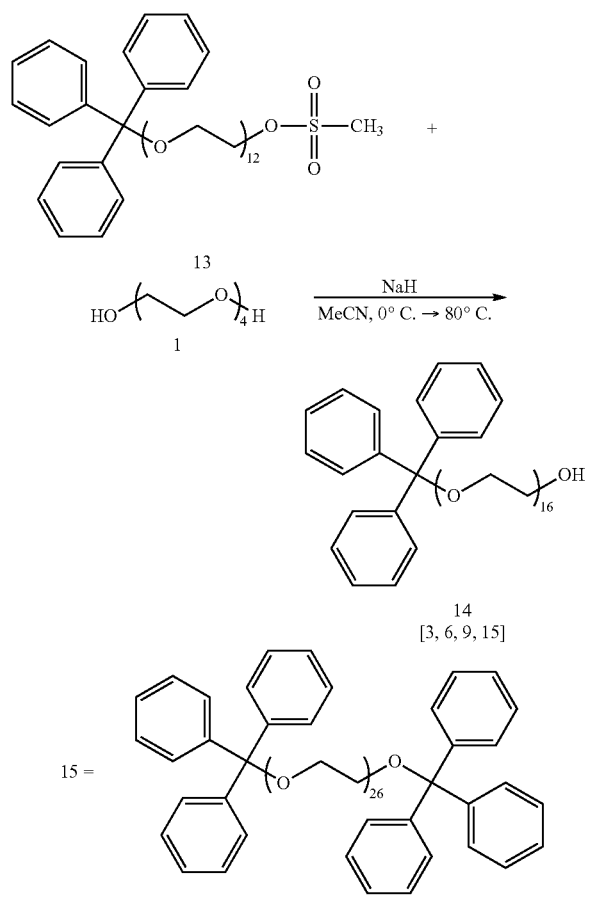

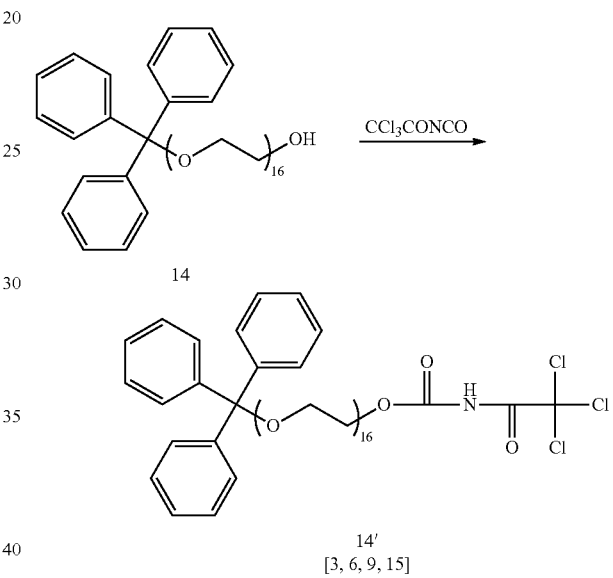

Figure 13:
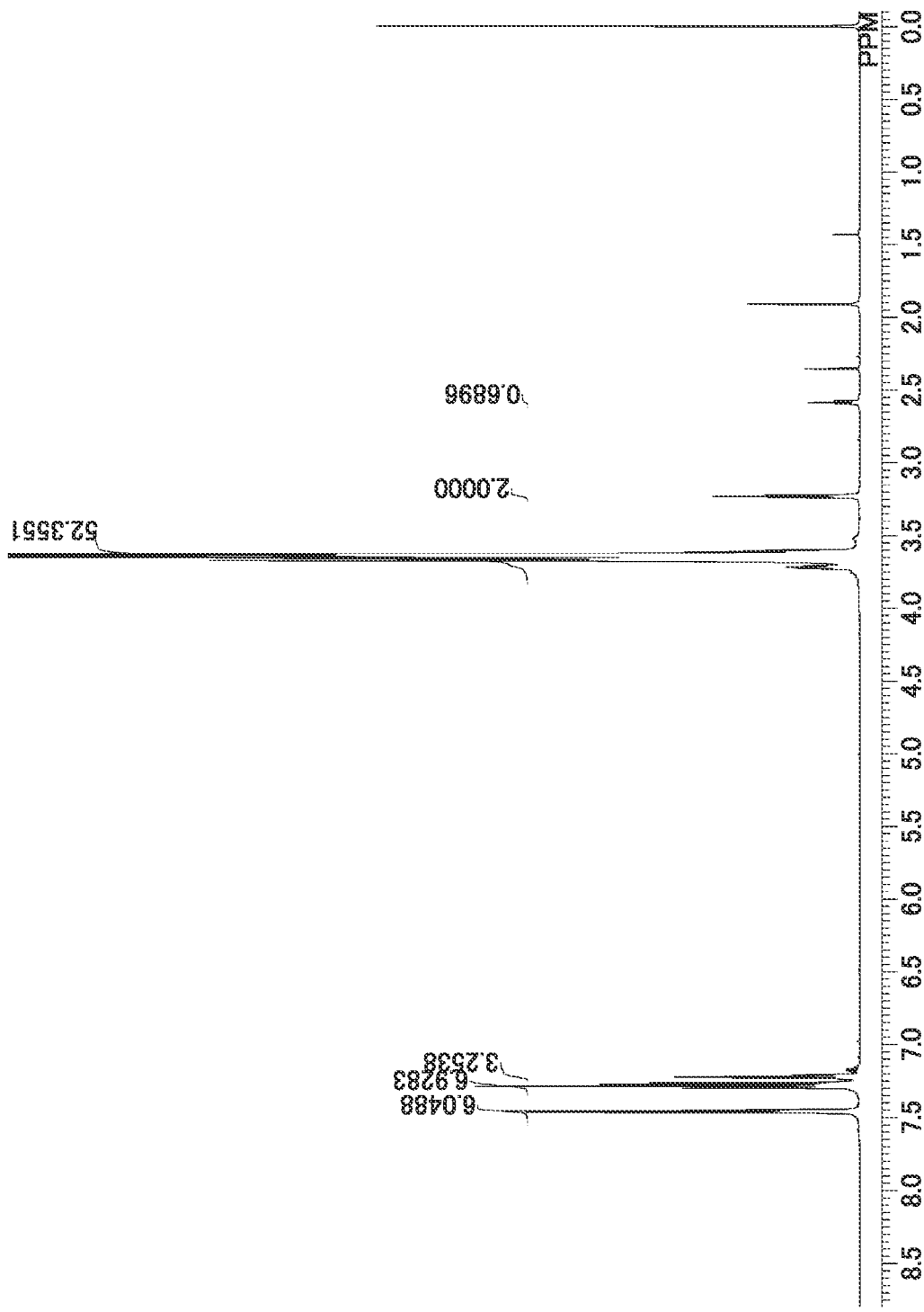
FIG. 13 shows results of NMR measurement of the compound 14 in Example 11.

Sodium hydride (6.3 g) was placed in a four-necked flask fitted with a cooling tube, a thermometer, and a nitrogen-inlet tube, and after the inside was replaced with nitrogen, 192 ml of MeCN was added, followed by cooling to 0° C. Tetraethylene glycol 1 (108 g, 0.56 mol) azeotropically dehydrated with 53 ml of toluene was mixed with 96 ml of MeCN and the resultant one was placed in a dropping funnel and added dropwise over a period of 30 minutes. After completion of the dropwise addition, the reaction product containing the compound 13 obtained in Example 10 (compound 13: 96 g, less than 0.11 mol) was mixed with 96 ml of MeCN, and the resultant one was placed in the same dropping funnel and added dropwise over a period of 15 minutes. After completion of dropwise addition, the reaction mixture was heated to 75° C. and stirred for 3 hours. After 3 hours, it was confirmed by $^1$H-NMR (CDCl$_3$) that the compound 13 disappeared, and the mixture was allowed to cool to 40° C. or lower. The reaction mixture was added with 170 ml of a saturated aqueous ammonium chloride solution and 146 ml of hexane, and the layers were separated. The hexane layer (upper layer) was removed and the lower layer was concentrated under reduced pressure, and 481 ml of toluene was added to the residue. This toluene solution was washed once with 260 ml of a saturated aqueous ammonium chloride solution and three times with 480 ml of a saturated saline solution. Sodium sulfate was added to the organic layer, which was dried and filtered. The filtrate was concentrated under reduced pressure to obtain a reaction product containing the compound 14 as a pale yellow transparent liquid. Further, it was confirmed by the results of TLC measurement and NMR measurement (FIG. 13) that the above compounds 3, 6, 9 and 15 were also contained in the obtained reaction product.

Figure 14:
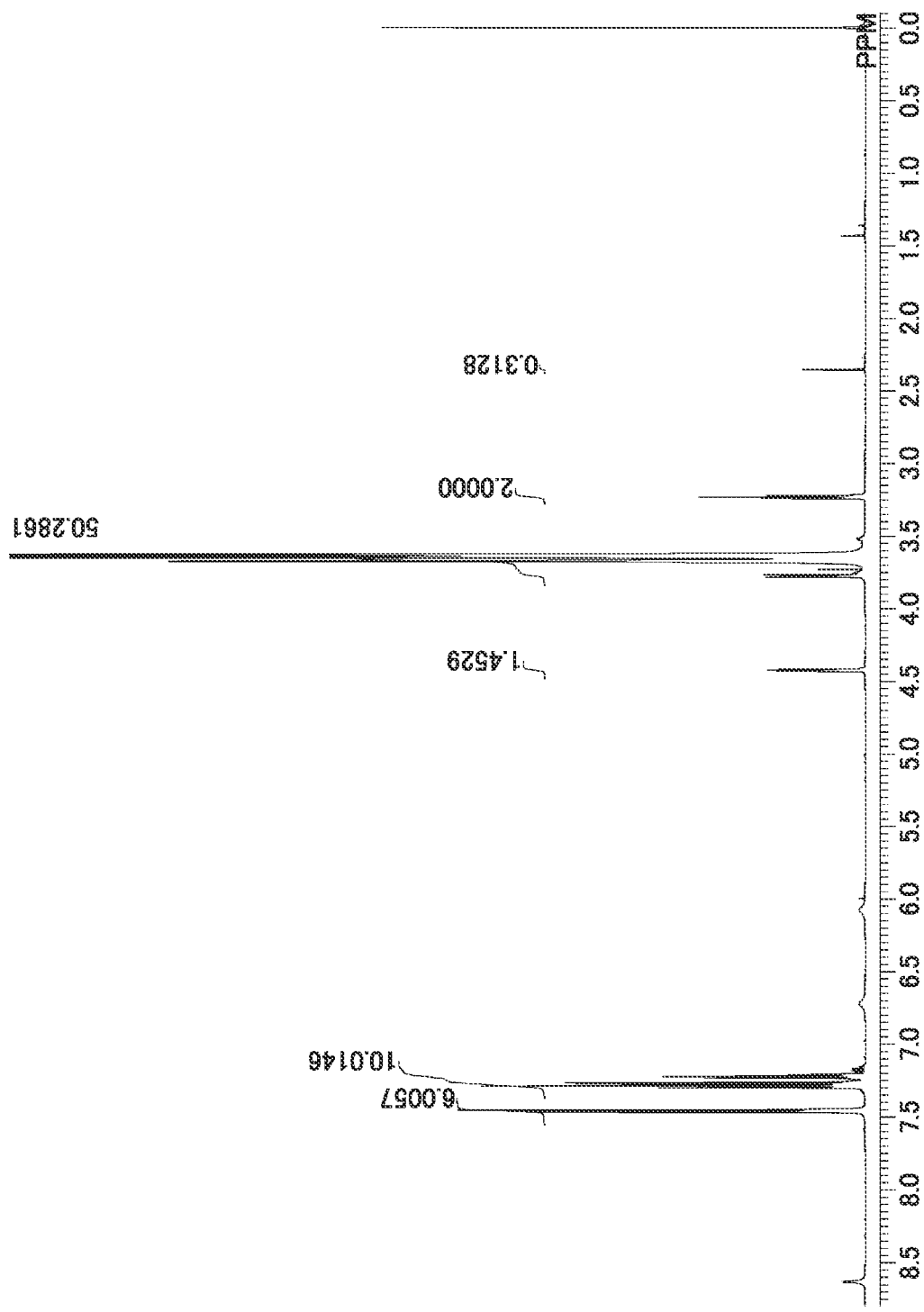
FIG. 14 shows results of NMR measurement of the compound 14' in Example 11.

Compound 14
$^1$H-NMR (CDCl$_3$, internal standard TMS); δ (ppm):
2.78 (1H, b, —C—(OCH$_2$CH$_2$)$_{16}$—OH,
3.23 (2H, t, (C$_6$H$_5$)$_3$C—OCH$_2$CH$_2$—, including those derived from compounds 3, 6, 9, 15),
3.45-3.85 (62H, m, —OCH$_2$CH$_2$—(OCH$_2$CH$_2$)$_{11}$—OH, including those derived from compounds 3, 6, 9, 11)
7.21-7.47 (15H, m, (C$_6$H$_5$)$_3$C—OCH$_2$CH$_2$—, including compounds 3, 6, 9, 15)
Yield: 103 g From the results of $^1$H-NMR measurement (FIG. 14) of the compound 14' in which the hydroxyl group was labelled by treating the obtained reaction product containing the compound 14 using trichloroacetyl isocyanate, it was confirmed that the compounds 3, 6, 9 and 15 were contained in an amount of about 19 mol % (compound 3: 7 mol %, compound 6: 5 mol %, compound 9: 3 mol %, compound 15: 4 mol %, rough estimation).

Calculation formula of contents of compounds 3, 6, 9, 15 based on the peak at δ 3.23:

$$(((2-[\delta 4.43])/4H)/([\delta 4.43]/2H))\times 100 (\text{mol }\%)$$

As the contents of the compounds 3, 6, 9, the numerical values in Examples 1, 3 and 5 were applied.

Compound 14'
$^1$H-NMR (CDCl$_3$, internal standard TMS); δ (ppm):
3.23 (2H, t, (C$_6$H$_5$)$_3$C—OCH$_2$CH$_2$—, including those derived from compounds 3, 6, 9, 15),
3.45-3.85 (60H, m, —OHCH$_2$CH$_2$—(OCH$_2$CH$_2$)$_{14}$—OCH$_2$CH$_2$—OCO—, including those derived from compounds 3, 6, 9, 15)
4.43 (2H, t, —OCH$_2$CH$_2$—OCO—NH—COCCl$_3$),
7.21-7.47 (15H, m, (C$_6$H$_5$)$_3$C—OCH$_2$—, including those derived from compounds 3, 6, 9, 15)

Example 12 Synthesis of Compound 16

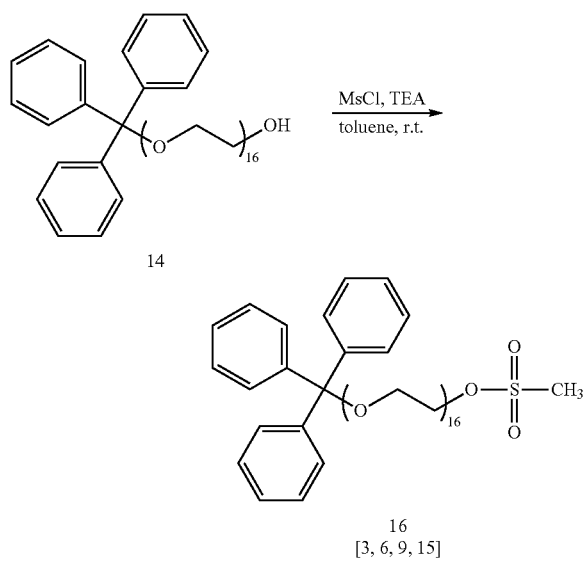

The reaction product containing the compound 14 synthesized in Example 11 (compound 14: 100 g, less than 0.10 mol) and toluene (500 ml) were placed in a four-necked flask fitted with a cooling tube, a thermometer, and a nitrogen-inlet tube, the inside of the flask was purged with nitrogen, and triethylamine (20 ml, 0.14 mol) was added. Methanesulfonyl chloride (9.6 ml, 0.12 mol) was added dropwise at 0° C., followed by stirring at room temperature for 2 hours. After 2 hours, the disappearance of the compound 14 was confirmed by TLC measurement, and 500 ml of a 5% aqueous sodium dihydrogen phosphate solution was added and the layers were separated. The organic layer was washed once with 500 ml of a 5% aqueous sodium dihydrogen phosphate solution, twice with 500 ml of a saturated aqueous sodium bicarbonate solution, and once with 500 ml of a saturated saline solution. Sodium sulfate was added to the organic layer, which was dried and filtered. The filtrate was concentrated under reduced pressure to obtain a reaction product containing the compound 16 as a pale yellow transparent liquid. Further, it was confirmed by TLC measurement and NMR measurement that the above compounds 3, 6, 9 and 15 were also contained in the obtained reaction product.

Yield: 106 g

Example 13 Synthesis of One-Terminal Trityl Group-Containing Monodispersed PEG (Compound 17) with Chain Length of 20

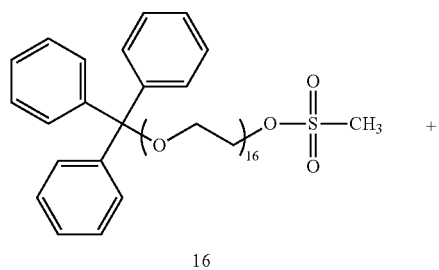

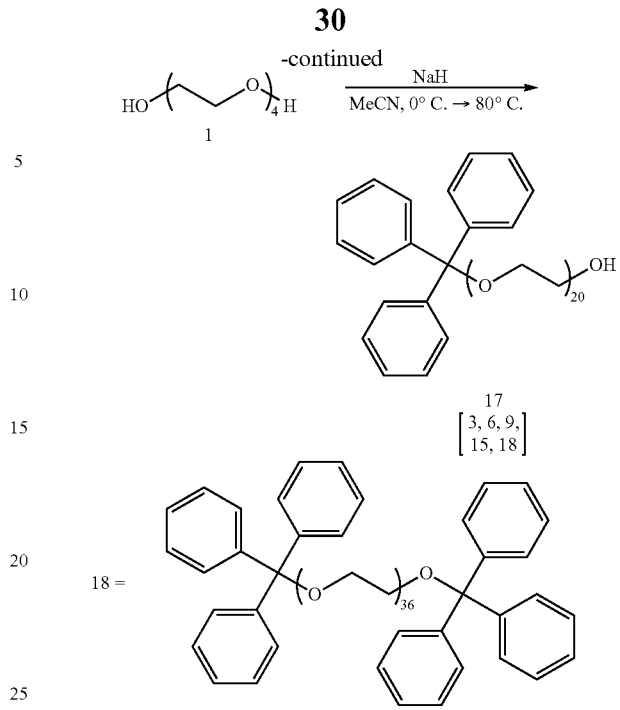

Figure 15:
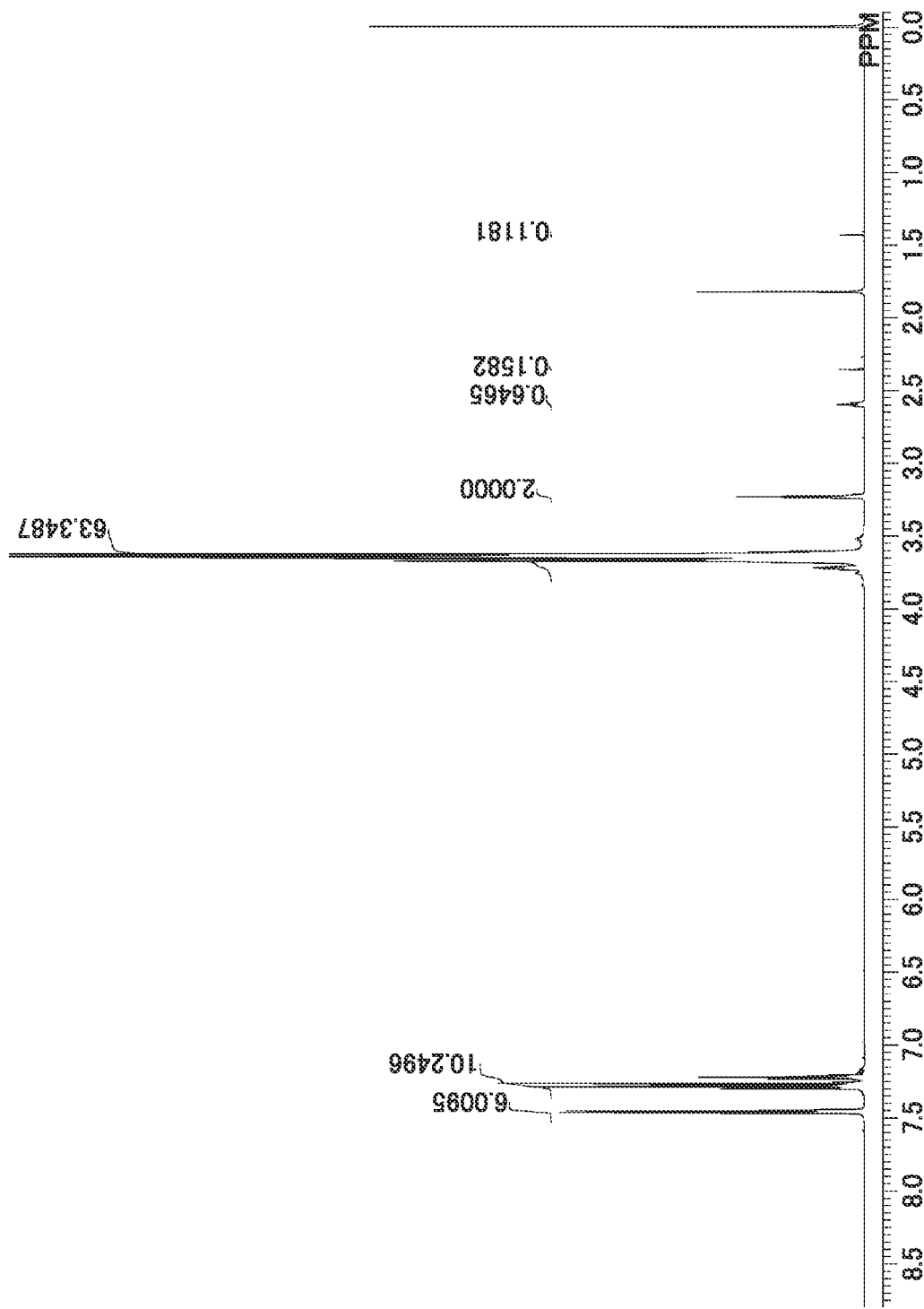
FIG. 15 shows results of NMR measurement of the compound 17 in Example 13.

Sodium hydride (5.7 g) was placed in a four-necked flask fitted with a cooling tube, a thermometer, and a nitrogen-inlet tube, and after the inside was replaced with nitrogen, 208 ml of MeCN was added, followed by cooling to 0° C. Tetraethylene glycol 1 (97 g, 0.5 mol) azeotropically dehydrated with 48 ml of toluene was mixed with 105 ml of MeCN, and the resultant one was placed in a dropping funnel and added dropwise over a period of 30 minutes. After completion of the dropwise addition, the reaction product containing the compound 16 obtained in Example 12 (compound 16: 109 g, less than 0.10 mol) was mixed with 105 ml of MeCN, and the resultant one was placed in the same dropping funnel and added dropwise over a period of 15 minutes. After completion of dropwise addition, the reaction mixture was heated to 75° C. and stirred for 3 hours. After 3 hours, it was confirmed by $^1$H-NMR (CDCl$_3$) that the compound 16 disappeared, and the mixture was allowed to cool to 40° C. or lower. The reaction mixture was added with 190 ml of a saturated aqueous ammonium chloride solution and 159 ml of hexane, and the layers were separated. The hexane layer (upper layer) was removed and the lower layer was concentrated under reduced pressure, and 524 ml of toluene was added to the residue. This toluene solution was washed once with 285 ml of a saturated aqueous ammonium chloride solution and three times with 520 ml of a saturated saline solution. Sodium sulfate was added to the organic layer, which was dried and filtered. The filtrate was concentrated under reduced pressure to obtain a reaction product containing the compound 17 as a pale yellow transparent liquid. Further, it was confirmed by the results of TLC measurement and NMR measurement (FIG. 15) that the above compounds 3, 6, 9, 15 and 18 were also contained in the obtained reaction product.

Compound 17

$^1$H-NMR (CDCl$_3$, internal standard TMS); δ (ppm):
2.64 (1H, b, —C—(OCH$_2$CH$_2$)$_{20}$—O$\underline{H}$,
3.23 (2H, t, (C$_6$H$_5$)$_3$C—OC$\underline{H}_2$CH$_2$—, including those derived from compounds 3, 6, 9, 15, 18),
3.45-3.85 (78H, m, —OCH$_2$C$\underline{H}_2$—(OC$\underline{H}_2$CH$_2$)$_{19}$—OH, including those derived from compounds 3, 6, 9, 15, 18)

7.21-7.47 (15H, m, $(C_6H_5)_3C$—$OCH_2CH_2$—, including compounds 3, 6, 9, 15, 18)

Yield: 109 g

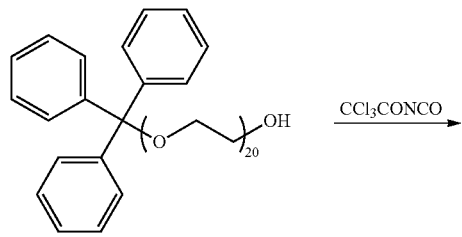

17

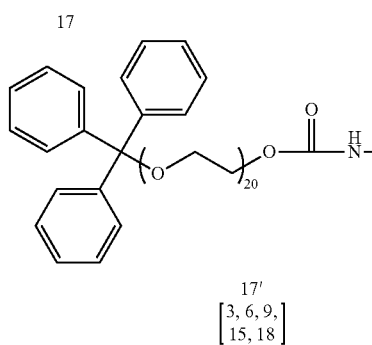

17'
$\begin{bmatrix} 3, 6, 9, \\ 15, 18 \end{bmatrix}$

Figure 16:
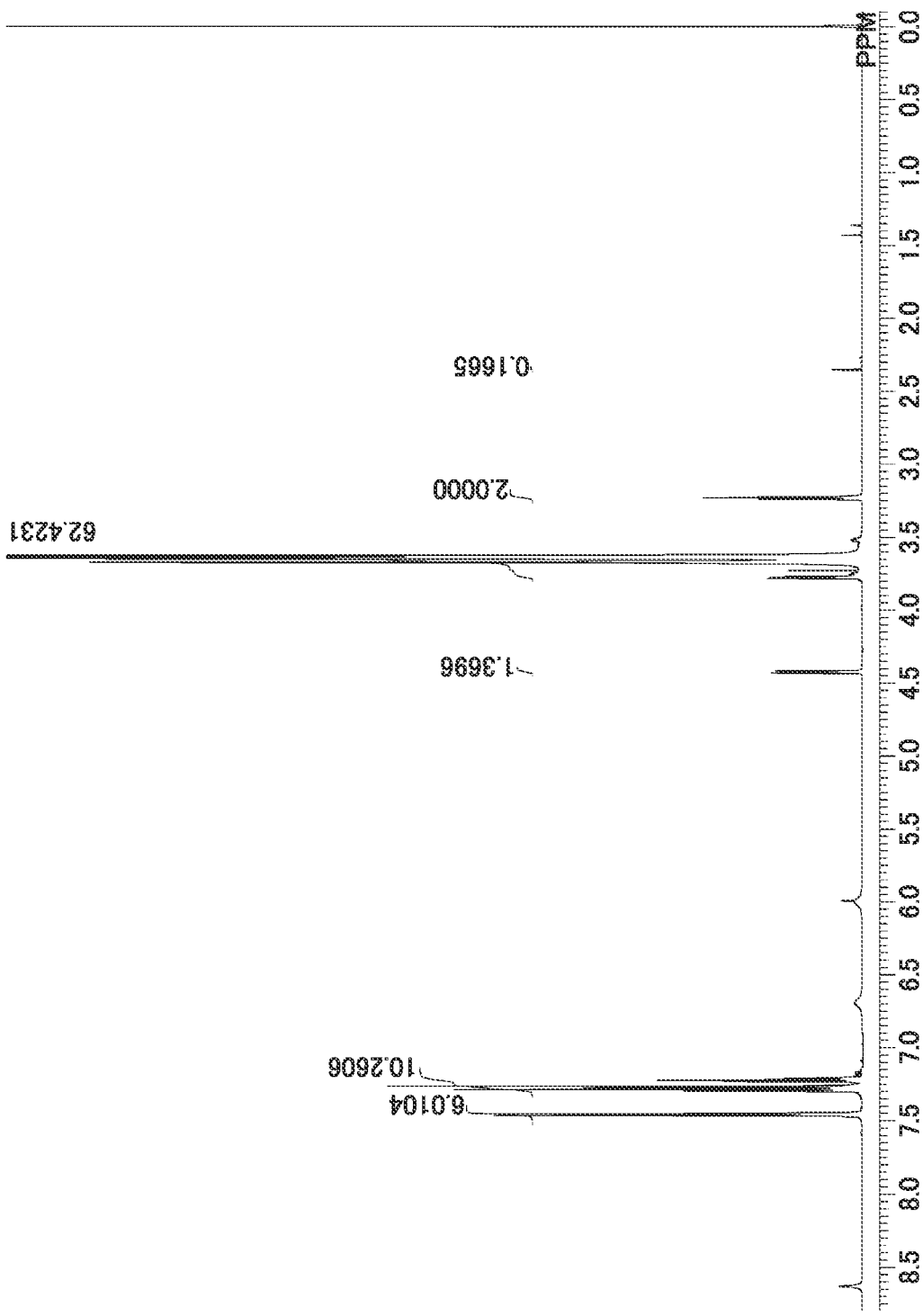
FIG. 16 shows results of NMR measurement of the compound 17' in Example 13.

From the results of $^1$H-NMR measurement (FIG. 16) of the compound 17' in which the hydroxyl group was labelled by treating the obtained reaction product containing the compound 17 using trichloroacetyl isocyanate, it was confirmed that the compounds 3, 6, 9, 15 and 18 were contained in an amount of about 23 mot % (compound 3: 7 mot %, compound 6: 5 mol %, compound 9: 3 mot %, compound 15: 4 mot %, compound 18: 4 mot %, rough estimation)

Calculation formula of contents of compounds 3, 6, 9, 15, 18 based on the peak at & 3.23:

(((2−[δ4.43])/4H)/([δ4.43]/2H))×100(mol %)

As the contents of the compounds 3, 6, 9, 15, the numerical values in Examples 1, 3, 5 and 11 were applied.

Compound 17'

$^1$H-NMR (CDCl$_3$, internal standard TMS); δ (ppm):

3.23 (2H, t, $(C_6H_5)_3C$—$OC\underline{H}_2CH_2$—, including those derived from compounds 3, 6, 9, 15, 18), 3.45-3.85 (76H, m, —$OCH_2C\underline{H}_2$—$(OC\underline{H}_2C\underline{H}_2)_{18}$—$OCH_2CH_2$—OCO—, including those derived from compounds 3, 6, 9, 15, 18)

4.43 (2H, t, —$OCH_2C\underline{H}_2$—OCO—NH—COCCl$_3$), 7.21-7.47 (15H, m, $(C_6H_5)_3C$—$OCH_2CH_2$—, including those derived from compounds 3, 6, 9, 15, 18)

Example 14 Synthesis of Compound 19

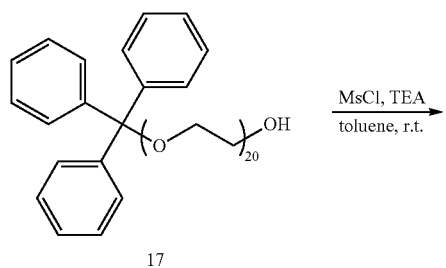

17

-continued

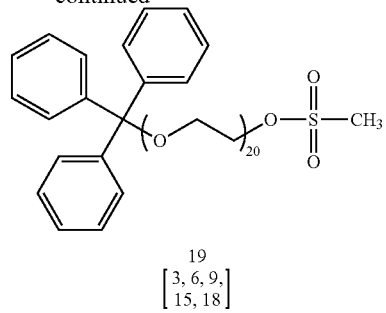

19
$\begin{bmatrix} 3, 6, 9, \\ 15, 18 \end{bmatrix}$

The reaction product containing the compound 17 synthesized in Example 13 (compound 17: 107 g, less than 0.094 mol) and toluene (535 ml) were placed in a four-necked flask fitted with a cooling tube, a thermometer, and a nitrogen-inlet tube, the inside of the flask was purged with nitrogen, and triethylamine (18 ml, 0.13 mol) was added. Methanesulfonyl chloride (8.7 ml, 0.11 mol) was added dropwise at 0° C., followed by stirring at room temperature for 2 hours. After 2 hours, the disappearance of the compound 17 was confirmed by TLC measurement, and 535 ml of a 5% aqueous sodium dihydrogen phosphate solution was added and the layers were separated. The organic layer was washed once with 535 ml of a 5% aqueous sodium dihydrogen phosphate solution, twice with 535 ml of a saturated aqueous sodium bicarbonate solution, and once with 535 ml of a saturated saline solution. Sodium sulfate was added to the organic layer, which was dried and filtered. The filtrate was concentrated under reduced pressure to obtain a reaction product containing the compound 19 as a pale yellow transparent liquid. Further, it was confirmed by TLC measurement and NMR measurement that the above compounds 3, 6, 9, 15 and 18 were also contained in the obtained reaction product.

Yield: 112 g

Example 15 Synthesis of One-Terminal Trityl Group-Containing Monodispersed PEG (Compound 20) with Chain Length of 24

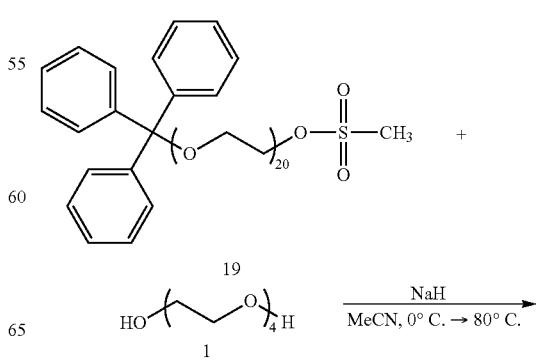

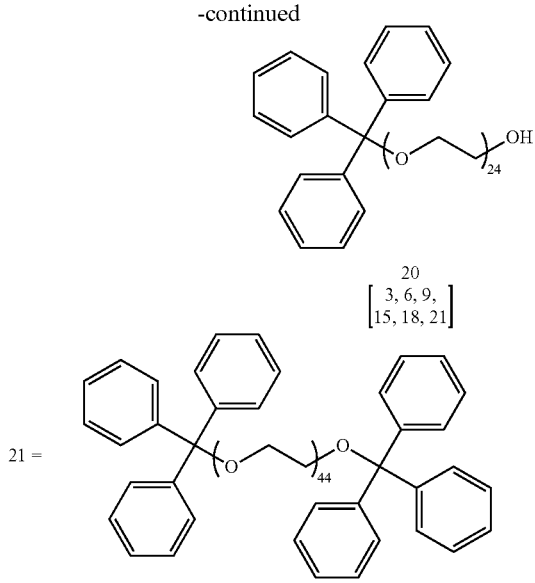

20
$\begin{bmatrix} 3, 6, 9, \\ 15, 18, 21 \end{bmatrix}$

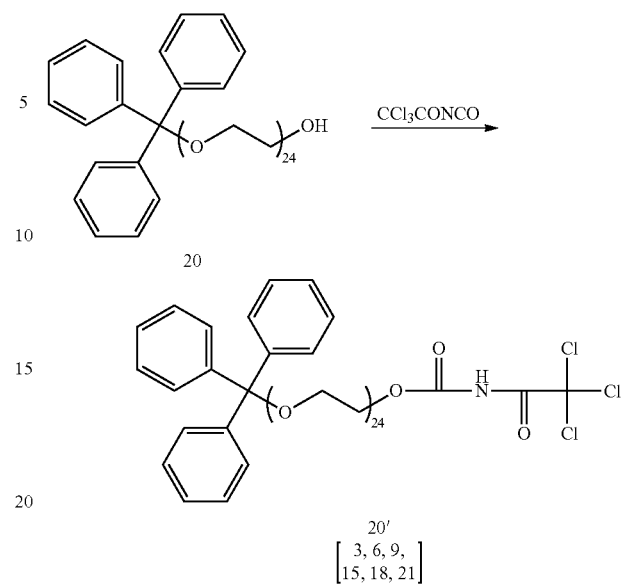

20

21 =

20'
$\begin{bmatrix} 3, 6, 9, \\ 15, 18, 21 \end{bmatrix}$

Figure 17:
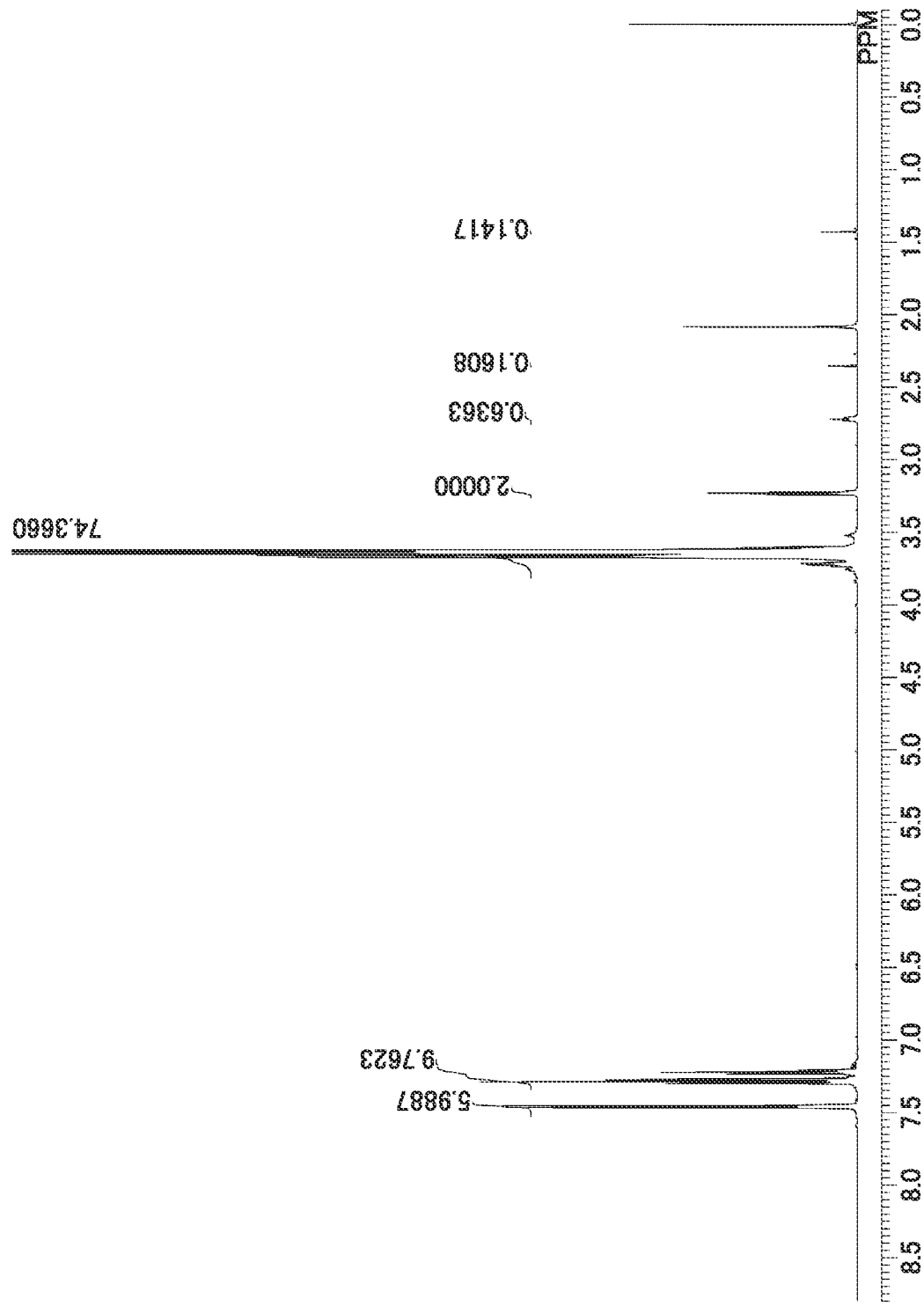
FIG. 17 shows results of NMR measurement of the compound 20 in Example 15.

Sodium hydride (5.2 g) was placed in a four-necked flask fitted with a cooling tube, a thermometer, and a nitrogen-inlet tube, and after the inside was replaced with nitrogen, 221 ml of MeCN was added, followed by cooling to 0° C. Tetraethylene glycol 1 (88 g, 0.46 mol) azeotropically dehydrated with 44 m of toluene was mixed with 111 ml of MeCN, and the resultant one was placed in a dropping funnel and added dropwise over a period of 30 minutes. After completion of the dropwise addition, the reaction product containing the compound 19 obtained in Example 14 (compound 19: 113 g, less than 0.092 mol) was mixed with 111 ml of MeCN, and the resultant one was placed in the same dropping funnel and added dropwise over a period of 15 minutes. After completion of dropwise addition, the reaction mixture was heated to 75° C. and stirred for 3 hours. After 3 hours, it was confirmed by $^1$H-NMR (CDCl$_3$) that the compound 19 disappeared, and the mixture was allowed to cool to 40° C. or lower. The reaction mixture was added with 200 ml of a saturated aqueous ammonium chloride solution and 168 ml of hexane, and the layers were separated. The hexane layer (upper layer) was removed and the lower layer was concentrated under reduced pressure, and 556 ml of toluene was added to the residue. This toluene solution was washed once with 300 ml of a saturated aqueous ammonium chloride solution and three times with 555 ml of a saturated saline solution. Sodium sulfate was added to the organic layer, which was dried and filtered. The filtrate was concentrated under reduced pressure to obtain a reaction product containing the compound 20 as a pale yellow transparent liquid. Further, it was confirmed by the results of TLC measurement and NMR measurement (FIG. 17) that the above compounds 3, 6, 9, 15, 18 and 21 were also contained in the obtained reaction product.

Figure 18:
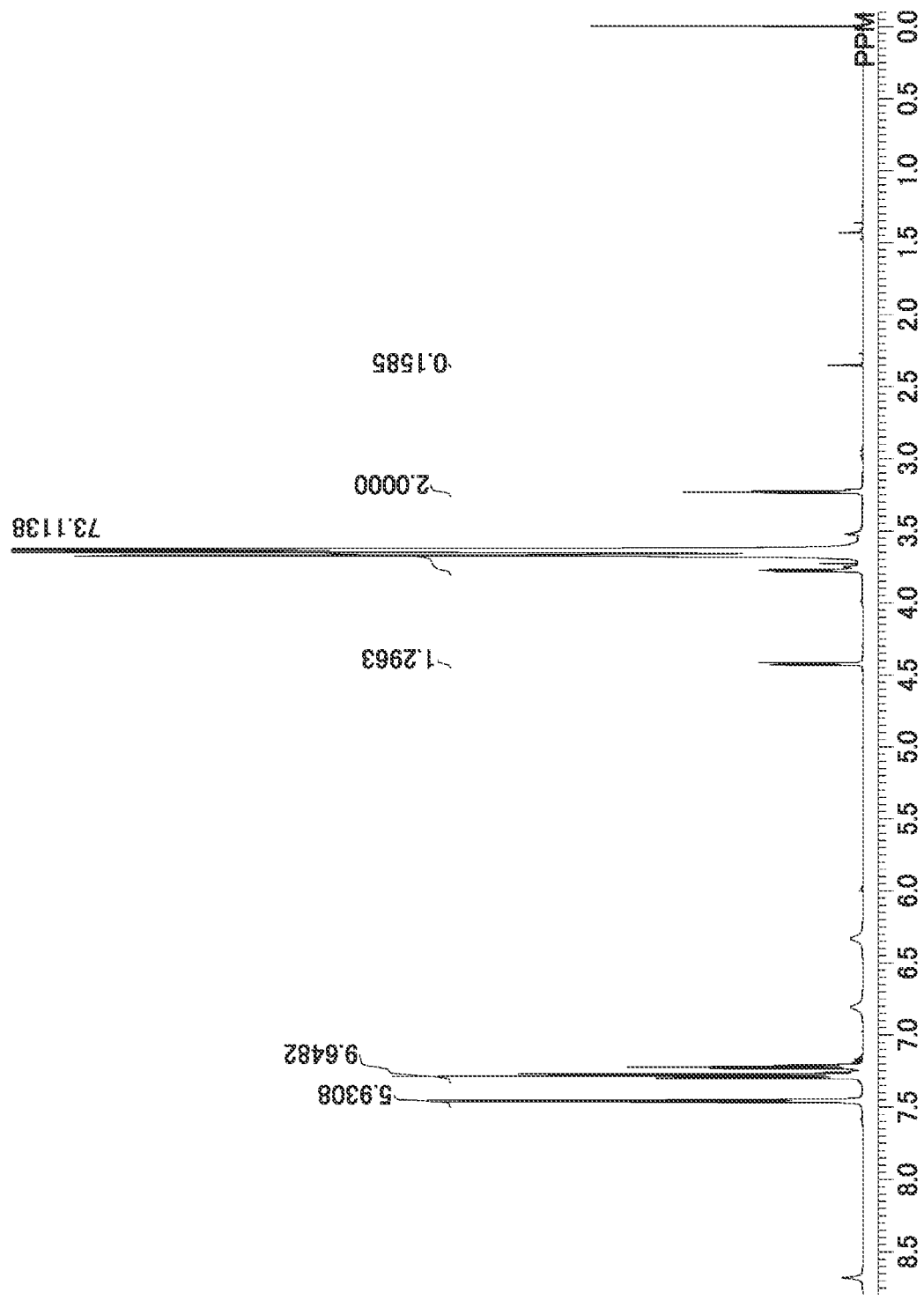
FIG. 18 shows results of NMR measurement of the compound 20' in Example 15.

Compound 20
$^1$H-NMR (CDCl$_3$, internal standard TMS); δ (ppm):
2.66 (1 H, b, —C—(OCH$_2$CH$_2$)$_{24}$—OH,
3.23 (2H, t, (C$_6$H$_5$)$_3$C—OCH$_2$CH$_2$—, including those derived from compounds 3, 6, 9, 15, 18, 21),
3.45-3.85 (94H, m, —OCH$_2$CH$_2$—(OCH$_2$CH$_2$)$_{23}$—OH, including those derived from compounds 3, 6, 9, 15, 18, 21)
7.21-7.47 (15H, m, (C$_6$H$_5$)$_3$C—OCH$_2$CH$_2$—, including compounds 3, 6, 9, 15, 18, 21)
Yield: 115 g From the results of $^1$H-NMR measurement (FIG. 18) of the compound 20' in which the hydroxyl group was labelled by treating the obtained reaction product containing the compound 20 using trichloroacetyl isocyanate, it was confirmed that the compounds 3, 6, 9, 15, 18 and 21 were contained in an amount of about 27 mol % (compound 3: 7 mol %, compound 6: 5 mol %, compound 9: 3 mol %, compound 15: 4 mol %, compound 18: 4 mot %, compound 21: 4 mol %, rough estimation).

Calculation formula of contents of compounds 3, 6, 9, 15, 18, 21 based on the peak at δ 3.23:

$$(((2-[\delta 4.43])/4H)/([\delta 4.43]/2H)) \times 100 (\text{mol \%})$$

As the contents of the compounds 3, 6, 9, 15, 18, the numerical values in Examples 1, 3, 5, 11 and 13 were applied.

Compound 20'
$^1$H-NMR (CDCl$_3$, internal standard TMS); δ (ppm):
3.23 (2H, t, (C$_6$H$_5$)$_3$C—OCH$_2$CH$_2$—, including those derived from compounds 3, 6, 9, 15, 18, 21),
3.45-3.85 (92H, m, —OCH$_2$CH$_2$—(OCH$_2$CH$_2$)$_{22}$—OCH$_2$CH$_2$—OCO—, including those derived from compounds 3, 6, 9, 15, 18, 21)
4.43 (2H, t, —OCH$_2$CH$_2$—OCO—NH—COCCl$_3$),
7.21-7.47 (15H, m, (C$_6$H$_5$)$_3$C—OCH$_{12}$CH$_2$—, including those derived from compounds 3, 6, 9, 15, 18, 21)

Example 16 Purification of One-Terminal Trityl Group-Containing Monodispersed PEG (Compound 20) with Chain Length of 24

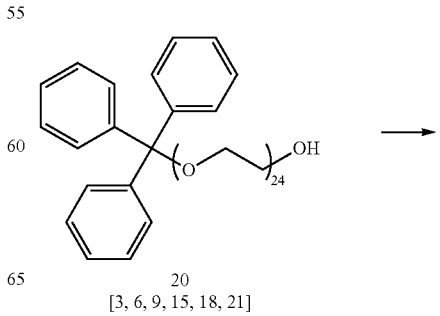

20
[3, 6, 9, 15, 18, 21]

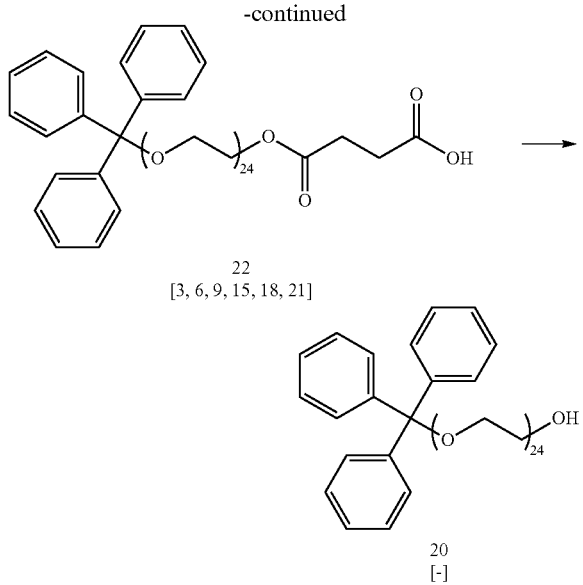

22
[3, 6, 9, 15, 18, 21]

20
[-]

Step (A)

A mixture containing the compound 20 as a main component (97 g, 74 mmol, including about 27 mol %, about 30% by mass of the ditritylated impurities 3, 6, 9, 15, 18, 21 in total from Example 15), sodium acetate (6.0 g, 74 mmol), and toluene (97 g) were added to a four-necked flask fitted with a cooling tube, a thermometer, and a nitrogen-inlet tube. The inside of the flask was purged with nitrogen, and succinic anhydride (11 g, 110 mmol) was added. The mixture was stirred at 70° C. for 4 hours. After 4 hours, the disappearance of the compound 20 was confirmed by TLC measurement, and the whole was cooled to 40° C. or lower. After adding toluene (155 g), a 23.4 wt % saline solution (582 g) was added, and liquid-separation washing was performed once at 55° C.

Step (B)

Hexane (33 g), methanol (226 g) and a phosphate (0.3 M) buffer of pH 6.8 (222 g) were charged into the organic layer to separate layers. It was confirmed that the pH of the cloudy aqueous layer was from 5 to 7, and the mixture was stirred at 45 to 50° C. for 15 minutes and then allowed to stand. The transparency of the upper and lower layers were confirmed, and the organic layer was discarded. Toluene (252 g) was added to the aqueous layer, and the mixture was stirred at 45 to 50° C. for 15 minutes and then allowed to stand. After separation into upper and lower layers, the organic layer was discarded. After liquid-separation washing was performed twice more, it was confirmed from TLC measurement that the spots derived from the ditritylated impurities (3, 6, 9, 15, 18, 21) disappeared.

Solvent Mass Ratio at the Time of Liquid-Separation Washing:

Organic solvent I:Organic solvent II:Organic solvent III=44.2%:49.3%:6.5%

Step (C)

After washing, a 400 g/L aqueous sodium hydroxide solution (19 g) was added to the aqueous layer (pH 6.68), and the mixture was stirred at 35° C. for 4 hours. From the TLC measurement of the aqueous layer (pH 11.3) after 4 hours, the disappearance of the compound 22 was confirmed.

Figure 19:
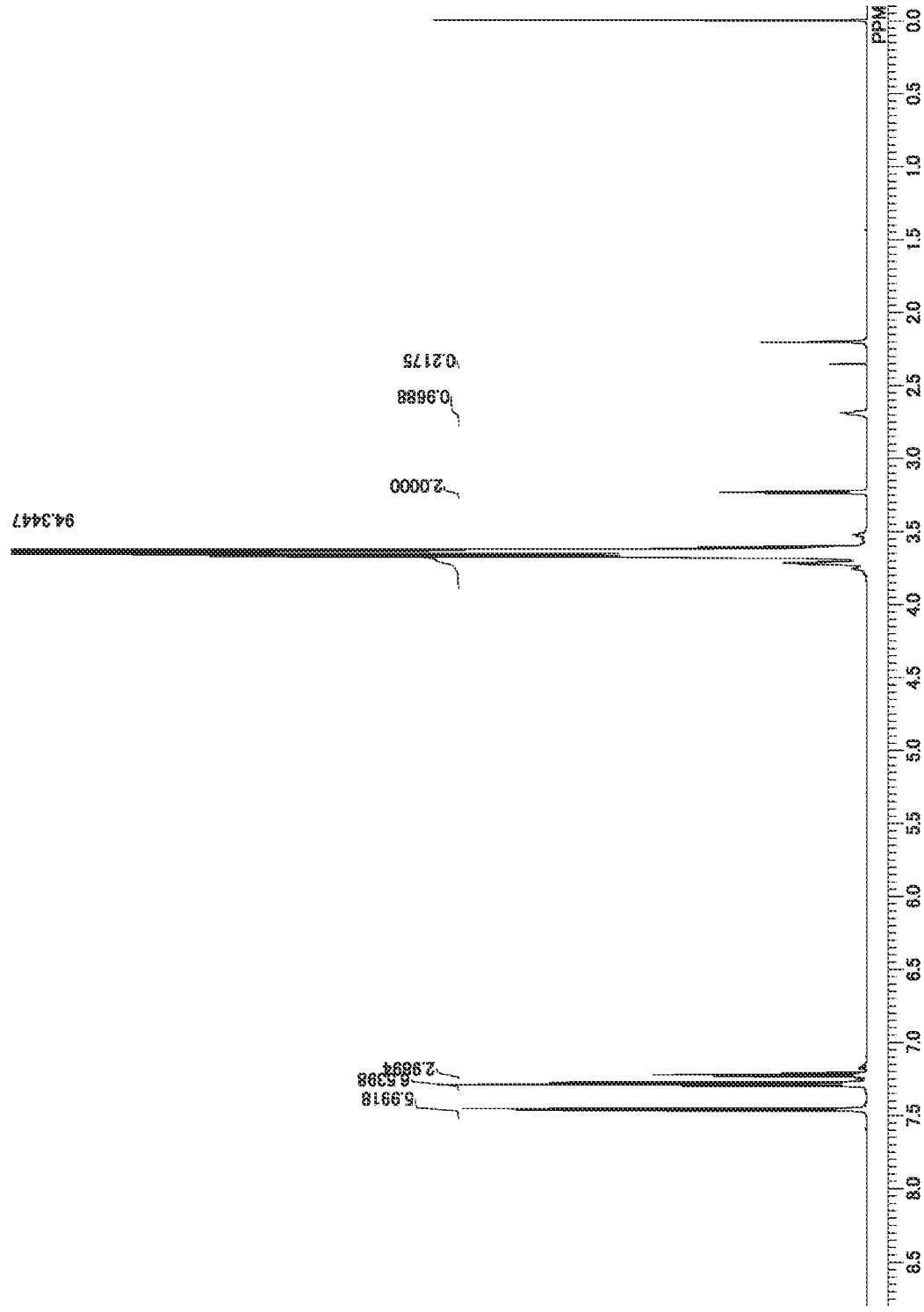
FIG. 19 shows results of NMR measurement of the compound 20 after purification in Example 16.
Figure 20:
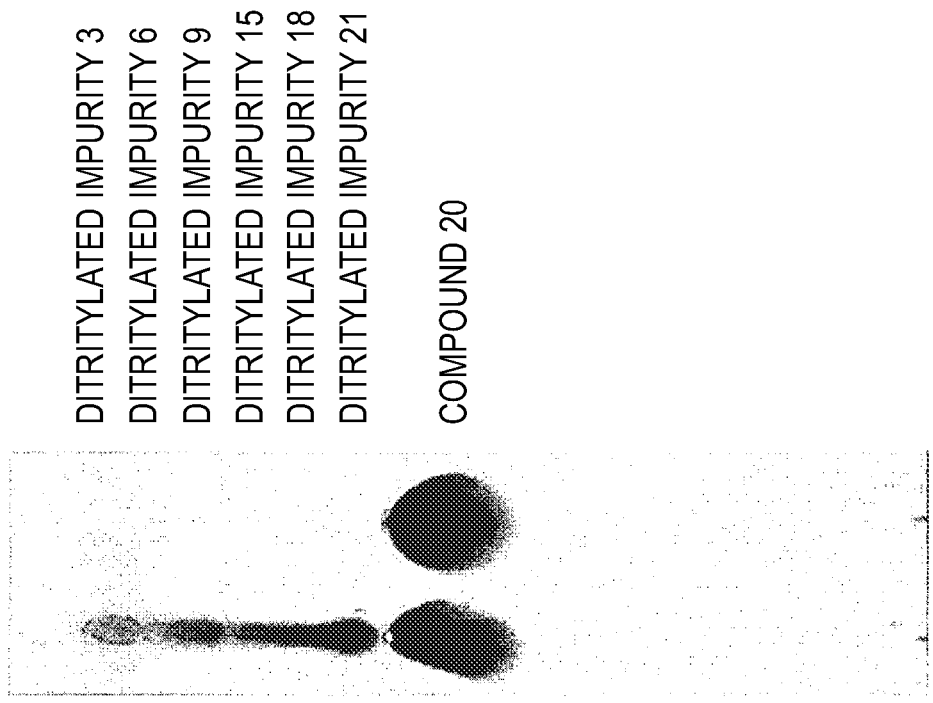
FIG. 20 shows a TLC chart of the compound 20 before and after purification in Example 16, the left showing before purification and the right showing after purification.

Dichloromethane (643 g) was added to the aqueous layer, and the mixture was stirred at 30° C. for 15 minutes. After the mixture was allowed to stand and layer separation was confirmed, it was confirmed from TLC measurement that the compound 20 did not remain in the aqueous layer, and the aqueous layer was discarded. A 20 wt % saline solution (582 g) was added to the organic layer, and liquid-separation washing was performed at 30° C. The collected organic layer was dehydrated with sodium sulfate (97 g), filtered using dichloromethane, and then concentrated to obtain the compound 20 (68 g). The integrated values of the results of NMR measurement were in agreement with the theoretical values (FIG. 19), and from the comparison of the TLC results of the compound 20 before and after purification, it was confirmed that no ditritylated impurity was contained (FIG. 20).

Ditritylated impurities N.D. (TLC measurement, see FIG. 20), yield 68 g, yield 70%

Compound 20 (after Purification)

$^1$H-NMR (CDCl$_3$, internal standard, TMS); δ (ppm):
2.69 (1H, s, —CH$_2$CH$_2$—(OCH$_2$CH$_2$)$_{23}$—O$\underline{H}$),
3.23 (2H, t, (C$_6$H$_5$)$_3$C—OC$\underline{H}_2$CH$_2$—),
3.45-3.85 (94H, m, —OCH$_2$C$\underline{H}_2$—(OC$\underline{H}_2$C$\underline{H}_2$)$_{23}$—OH)
7.21-7.47 (15H, m, (C$_6$$\underline{H}_5$)$_3$C—OCH$_2$CH$_2$—)

From the above Examples 6 to 9 and 16, it was explained that the ditritylated impurities can be removed from the one-terminal trityl group-containing monodispersed PEG immediately after the chain extension step.

Further, in Example 9, it was explained that, although the ditritylated impurities can be removed, but the number of liquid-separation washing times required for removing the ditritylated impurities increases, and the yield decreases as compared with the case of Example 7.

Comparative Example 1 Example where pH of Aqueous Solution is Too High

The same operations as in the step (A) of Example 7 were performed, and liquid-separation extraction was carried out so that the solvent ratio in the step (B) became as follows: a sodium bicarbonate (4 wt %, pH 8) aqueous solution (232 g), methanol (232 g), toluene (378 g), and hexane (145 g). The pH of the aqueous solution is 8, which is outside the range of the present invention.

It was confirmed from TLC measurement that the spots derived from ditritylated impurities (3, 6, 9) disappeared after liquid-separation extraction was carried out four times. However, during the liquid-separation extraction, the compound 10 was hydrolyzed to become the compound 8, which was extracted into the organic layer and lost.

In the step (C), the same operations as in Example 1 were carried out to obtain the compound 8 (53 g). The integrated values of the results of NMR measurement were in agreement with the theoretical values, and it was confirmed from the comparison of TLC results of the compound 8 before and after purification that no ditritylated impurity was contained.

Ditritylated impurities N.D., yield 53 g, yield 45%

INDUSTRIAL APPLICABILITY

According to the present invention, there is provided a novel purification method capable of obtaining a highly pure monodispersed PEG suitable for pharmaceutical use.

While the invention has been described in detail and with reference to specific embodiments thereof, it will be apparent to one skilled in the art that various changes and modifications can be made therein without departing from the spirit and scope thereof.

The present application is based on Japanese Patent Application No. 2018-63421 filed on Mar. 29, 2018, and the contents are incorporated herein by reference.

The invention claimed is:

1. A method for purifying a trityl group-containing monodispersed polyethylene glycol, which includes, from a mixture containing a trityl group-containing monodispersed polyethylene glycol represented by the following formula (1) and a ditritylated impurity represented by the following formula (2), separating and removing the ditritylated impurity to obtain the trityl group-containing monodispersed polyethylene glycol, the method comprising: performing steps (A), (B) and (C) in this order:

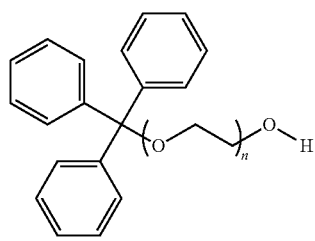
(1)

wherein, in the formula (1), n is a number of repeating units of an ethylene oxide unit and is 3 or more and 48 or less;

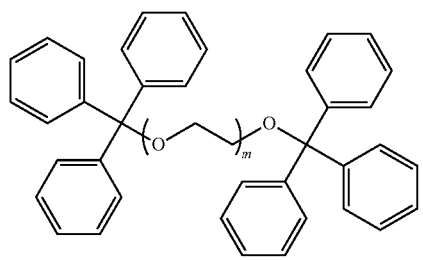
(2)

wherein, in the formula (2), m is a number of repeating units of an ethylene oxide unit and is 3 or more and 92 or less;

Step (A): a step of obtaining a reaction solution containing an ester compound having an ester structure and a carboxyl group by reacting a hydroxyl group of the trityl group-containing monodispersed polyethylene glycol represented by the formula (1) with a dibasic acid anhydride in the following organic solvent II, Step (B): an extraction step of separating an aqueous layer and an organic layer, partitioning the ditritylated impurity represented by the formula (2) into the organic layer and partitioning the ester compound into the aqueous layer by performing liquid-separation extraction purification using the reaction solution obtained in the step (A), one or more organic solvents selected from the group consisting of the following organic solvents I, II and III, and an aqueous solution having a pH of 3 to 7, Step (C): a step of performing hydrolysis of the ester compound by adding a base to the aqueous layer to obtain the trityl group-containing monodispersed polyethylene glycol:

Organic solvent I: an alcohol solvent having 3 or less carbon atoms,

Organic solvent II: an aromatic hydrocarbon solvent having 8 or less carbon atoms in total, Organic solvent III: a saturated aliphatic hydrocarbon solvent having 10 or less carbon atoms in total.

2. The method according to claim 1, wherein in the step (A), the dibasic acid anhydride is selected from the group consisting of succinic anhydride and glutaric anhydride.

3. The method according to claim 1, wherein in the step (B), the organic solvent I is one or more solvents selected from methanol, ethanol and propanol, the organic solvent II is one or more solvents selected from the group consisting of toluene and xylene, and the organic solvent III is one or more solvents selected from the group consisting of pentane, hexane and heptane.

4. The method according to claim 1, wherein with regard to the mixing ratio of the organic solvent in the step (B), the mass ratio of the organic solvent I is from 15 to 55% by mass, the mass ratio of the organic solvent II is from 15 to 75% by mass, and the mass ratio of the organic solvent III is from 0 to 50% by mass.

5. The method according to claim 1, wherein a temperature during the extraction step of the step (B) is 0° C. or higher and 60° C. or lower.

6. The method according to claim 1, wherein the extraction step of the step (B) is repeated.

7. The method according to claim 1, wherein the base in the step (C) is one or more bases selected from the group consisting of sodium hydroxide and potassium hydroxide.

8. The method according to claim 2, wherein in the step (B), the organic solvent I is one or more solvents selected from methanol, ethanol and propanol, the organic solvent II is one or more solvents selected from the group consisting of toluene and xylene, and the organic solvent III is one or more solvents selected from the group consisting of pentane, hexane and heptane.

9. The method according to claim 2, wherein with regard to the mixing ratio of the organic solvent in the step (B), the mass ratio of the organic solvent I is from 15 to 55% by mass, the mass ratio of the organic solvent II is from 15 to 75% by mass, and the mass ratio of the organic solvent III is from 0 to 50% by mass.

10. The method according to claim 3, wherein with regard to the mixing ratio of the organic solvent in the step (B), the mass ratio of the organic solvent I is from 15 to 55% by mass, the mass ratio of the organic solvent II is from 15 to 75% by mass, and the mass ratio of the organic solvent III is from 0 to 50% by mass.

11. The method according to claim 8, wherein with regard to the mixing ratio of the organic solvent in the step (B), the mass ratio of the organic solvent I is from 15 to 55% by mass, the mass ratio of the organic solvent II is from 15 to 75% by mass, and the mass ratio of the organic solvent III is from 0 to 50% by mass.

12. The method according to claim 2, wherein a temperature during the extraction step of the step (B) is 0° C. or higher and 60° C. or lower.

13. The method according to claim 3, wherein a temperature during the extraction step of the step (B) is 0° C. or higher and 60° C. or lower.

14. The method according to claim 8, wherein a temperature during the extraction step of the step (B) is 0° C. or higher and 60° C. or lower.

15. The method according to claim 2, wherein the extraction step of the step (B) is repeated.

16. The method according to claim 3, wherein the extraction step of the step (B) is repeated.

17. The method according to claim 8, wherein the extraction step of the step (B) is repeated.

18. The method according to claim 2, wherein the base in the step (C) is one or more bases selected from the group consisting of sodium hydroxide and potassium hydroxide.

19. The method according to claim 3, wherein the base in the step (C) is one or more bases selected from the group consisting of sodium hydroxide and potassium hydroxide.

20. The method according to claim 8, wherein the base in the step (C) is one or more bases selected from the group consisting of sodium hydroxide and potassium hydroxide.

* * * * *